United States Patent [19]
Meinzer et al.

[11] Patent Number: 5,782,805
[45] Date of Patent: Jul. 21, 1998

[54] MEDICAL INFUSION PUMP

[76] Inventors: Randolph Meinzer, 1703 Spruce St., Spring Grove, Ill. 60081; Grace M. Esche, 603 Gaslight Dr., Algonquin, Ill. 60102; Eric J. Michael, 533 Surryse Rd., Lake Zurich, Ill. 60047; Kimball J. Knowlton, 21793 Brentwood La., Lake Villa, Ill. 60046; Cynthia Bennett, 113 Arthur, Park Ridge, Ill. 60068; Eric Linner, 762 Village Rd., Crystal Lake, Ill. 60014; Kenneth M. Lynn, 2506 Amanda Dr., Spring Grove, Ill. 60081; Joseph Kruft, 818 E. Saratoga Cir., Island Lake, Ill. 60042; Eileen D. Hirotsuka, 211 W. Maple St., McHenry, Ill. 60050; Daniel Kusswurm, 1140 Appleton La., Geneva, Ill. 60134; Jane M. Zeisloft, 25570 N. Wagon Wheel Ct., Barrington, Ill. 60010; Janice Stewart, 203 N. Schoenbeck Rd., Prospect Heights, Ill. 60070; Debra Gelhar, 320 Cromwell Ct., Westmont, Ill. 60559; Gilbert Rivas, 267 Big Terra La., Gurnee, Ill. 60031

[21] Appl. No.: 631,819

[22] Filed: Apr. 10, 1996

[51] Int. Cl.$^6$ .................................................. A61M 37/00
[52] U.S. Cl. .................................... 604/131; 604/67; 604/151
[58] Field of Search ............................... 604/65–67, 131, 604/151, 245, 246

[56] References Cited

U.S. PATENT DOCUMENTS

| | | | |
|---|---|---|---|
| 4,553,958 | 11/1985 | LeCocq | 604/67 |
| 4,653,010 | 3/1987 | Figler et al. | 364/502 |
| 4,756,706 | 7/1988 | Kerns et al. | 604/66 |
| 4,854,324 | 8/1989 | Hirschman et al. | 128/655 |
| 4,898,578 | 2/1990 | Rubalcaba, Jr. | 604/66 |
| 4,946,439 | 8/1990 | Eggers | 604/67 |
| 5,041,086 | 8/1991 | Koenig et al. | 604/65 |
| 5,088,981 | 2/1992 | Howson et al. | 604/31 |
| 5,181,910 | 1/1993 | Scanlon | 604/67 |
| 5,207,642 | 5/1993 | Orkin et al. | 604/65 |
| 5,276,610 | 1/1994 | Maeda et al. | 364/413.02 |
| 5,298,021 | 3/1994 | Sherer | 604/66 |
| 5,304,127 | 4/1994 | Kawahara et al. | 604/65 |
| 5,368,562 | 11/1994 | Blomquist et al. | 604/65 |
| 5,378,231 | 1/1995 | Johnson et al. | 604/67 |
| 5,389,071 | 2/1995 | Kawahara et al. | 604/51 |
| 5,505,696 | 4/1996 | Miki | 604/67 |
| 5,507,412 | 4/1996 | Ebert et al. | 222/63 |
| 5,522,798 | 6/1996 | Johnson et al. | 604/65 |
| 5,547,470 | 8/1996 | Johnson et al. | 604/67 |
| 5,616,124 | 4/1997 | Hague et al. | 604/67 X |

FOREIGN PATENT DOCUMENTS

| | | | |
|---|---|---|---|
| 0 154 191 A1 | 9/1985 | European Pat. Off. | A61M 5/14 |
| 0 164 904 A2 | 12/1985 | European Pat. Off. | A61M 5/14 |
| 0 275 214 (A2 A3) | 7/1988 | European Pat. Off. | A61M 5/14 |
| 0-473-240-A2 | 8/1988 | European Pat. Off. | A61M 5/168 |
| 0 319 272 (A3) | 6/1989 | European Pat. Off. | A61M 5/14 |
| 0 319 272 A2 | 6/1989 | European Pat. Off. | A61M 5/14 |
| 0 398 583 (A2 A3) | 11/1990 | European Pat. Off. | A61M 5/142 |

(List continued on next page.)

*Primary Examiner*—Wynn Wood Coggins
*Assistant Examiner*—Deborah Blyveis
*Attorney, Agent, or Firm*—Francis C. Kowalik; Paul E. Schaafsma

[57] ABSTRACT

The present invention provides an infusion pump having a main body portion. The main body portion includes a display area for displaying user interface information. At least one pump module is provided which is removably secured to the main body portion and adapted to receive an IV tube. The pump module can apply pumping action to the IV tube. The pump module further includes an auxiliary display area for displaying supplemental user interface information. A microprocessor is contained in the main body portion for generating user interface information on the display areas.

46 Claims, 32 Drawing Sheets

FOREIGN PATENT DOCUMENTS

| | | |
|---|---|---|
| 0 503 670 (A2 A3) | 9/1992 | European Pat. Off. ....... A61M 5/172 |
| 0 589 356 A2 | 3/1994 | European Pat. Off. ....... A61M 5/145 |
| 0 595 474 (A2 A3) | 5/1994 | European Pat. Off. ....... A61M 5/145 |
| 0 681 847 | 11/1995 | European Pat. Off. ....... A61M 5/142 |
| 43 20 365 | 12/1994 | Germany ........................... B01J 4/00 |
| 43 33 266 | 3/1995 | Germany ..................... A61M 5/175 |
| WO 92/15349 | 9/1992 | WIPO ........................... A61M 5/172 |
| WO 93/04713 | 3/1993 | WIPO ........................... A61M 5/168 |
| WO 93/14807 | 8/1993 | WIPO ........................... A61M 31/00 |
| WO 93/24893 | 12/1993 | WIPO ........................... G06F 15/42 |
| WO 94/08647 | 4/1994 | WIPO ............................. A61M 5/16 |
| WO 94/12235 | 6/1994 | WIPO ........................... A61M 31/00 |
| WO 95/24229 | 9/1995 | WIPO . |
| WO 96/20745 | 7/1996 | WIPO ........................... A61M 5/172 |
| WO 96/28209 | 9/1996 | WIPO ........................... A61M 37/00 |
| WO 96/36389 | 11/1996 | WIPO ........................... A61M 31/00 |

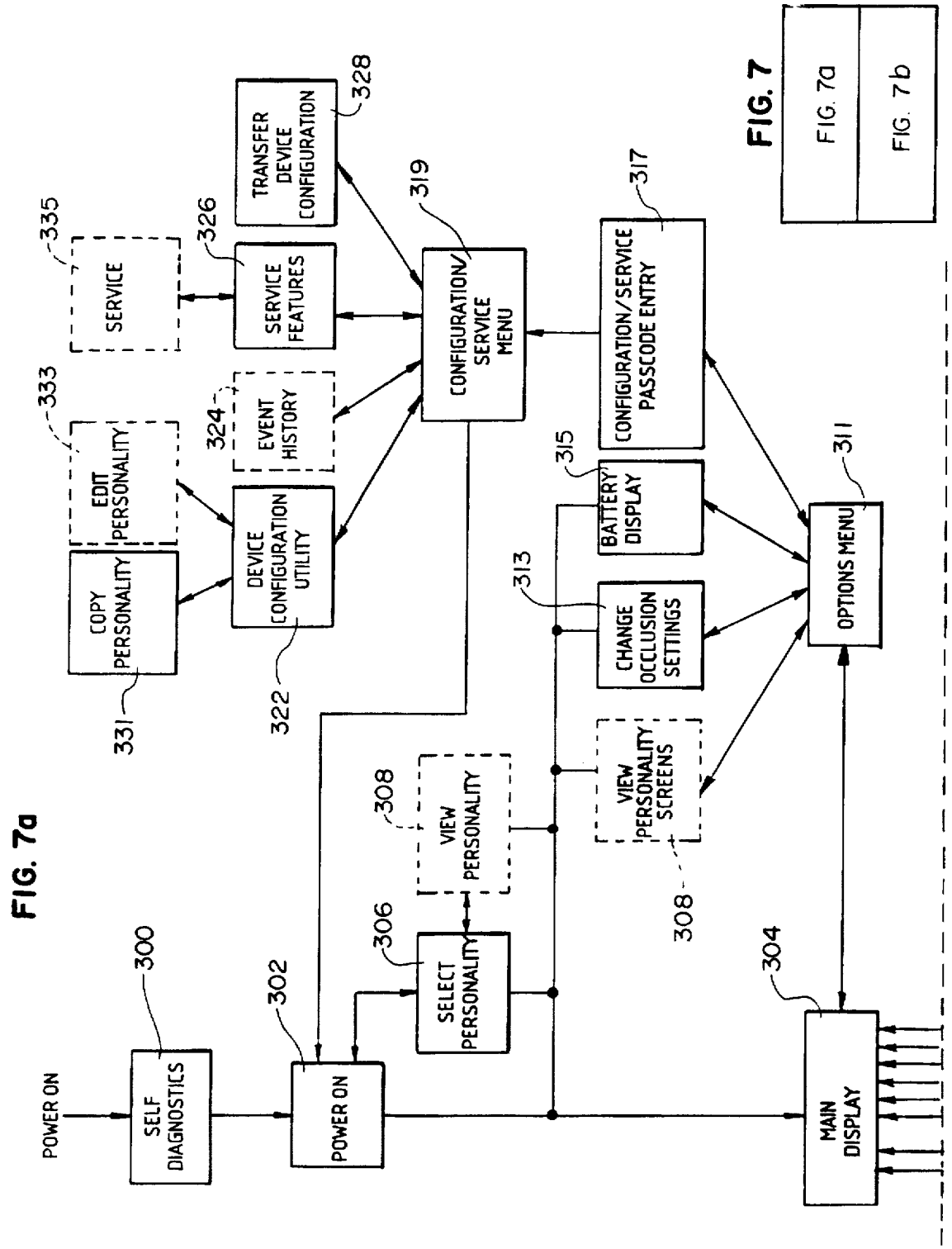

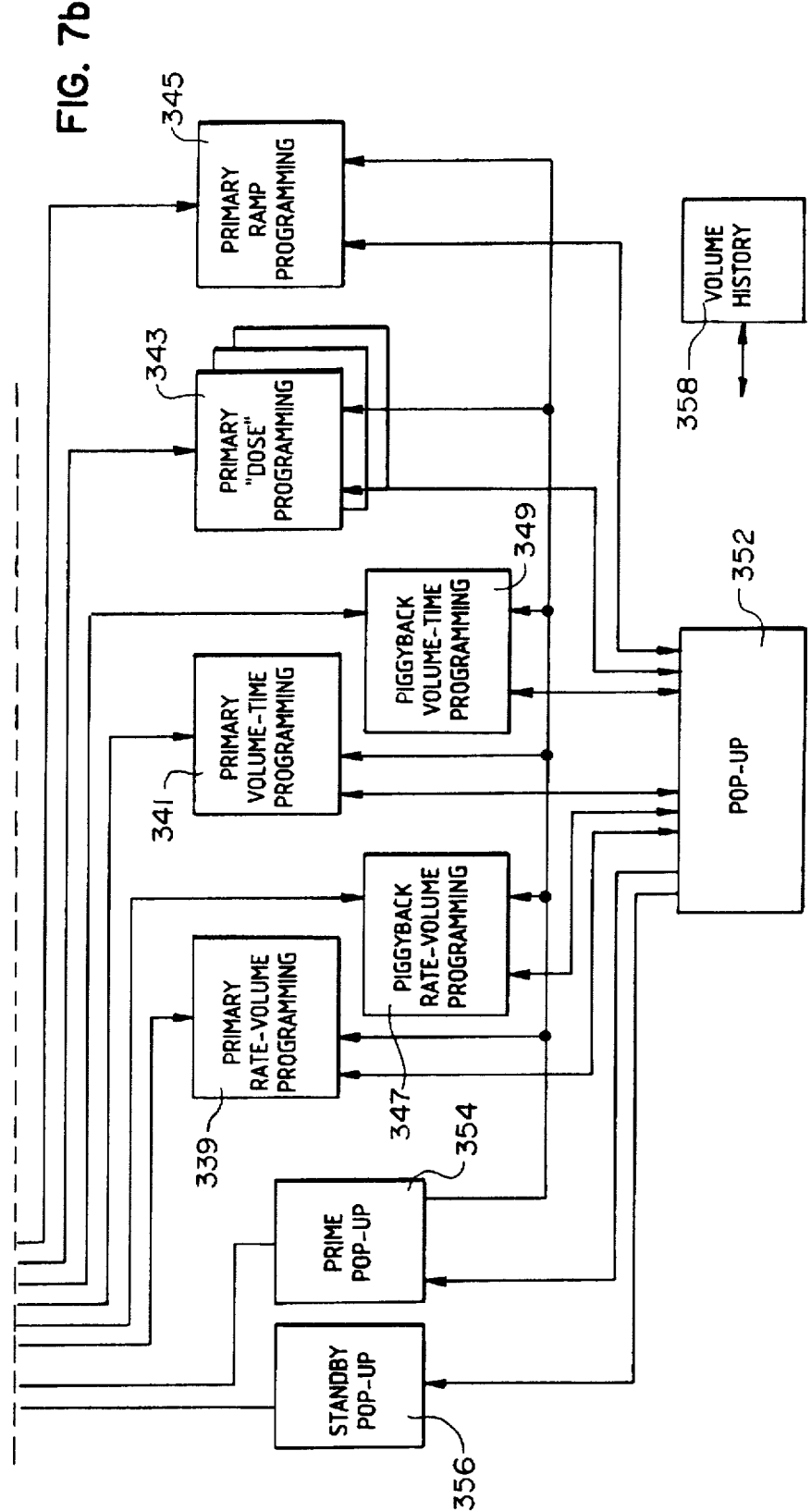

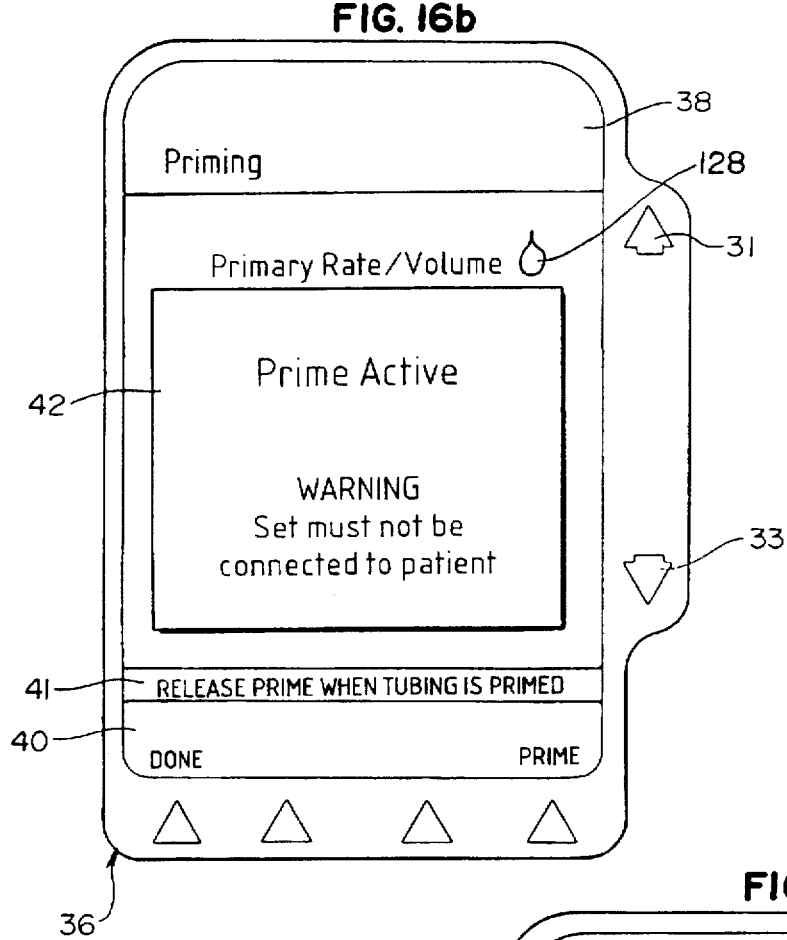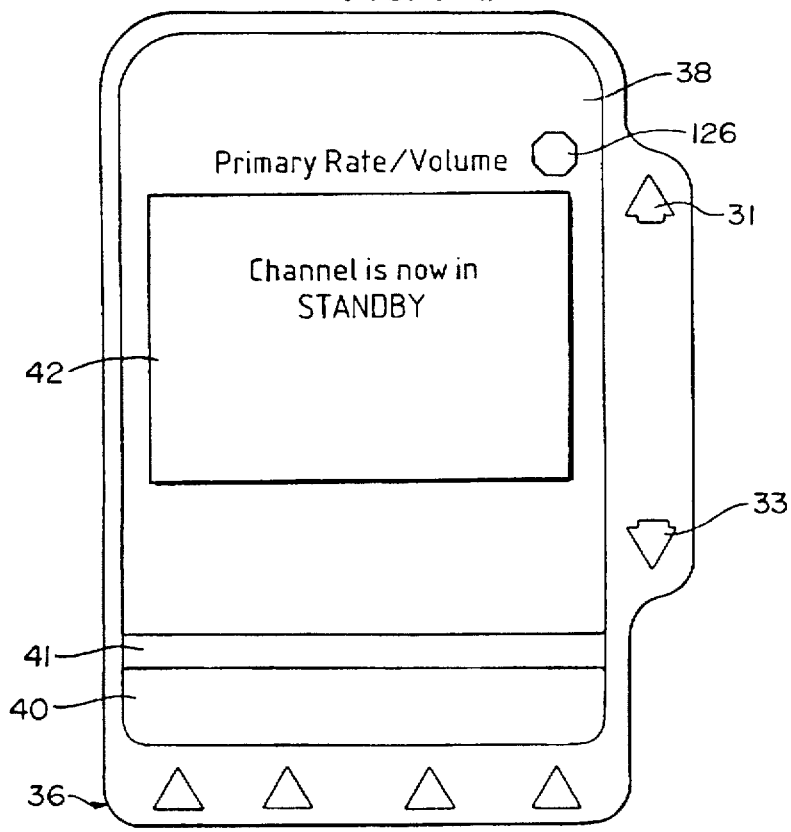

MEDICAL INFUSION PUMP

FIELD OF THE INVENTION

The present invention relates to medical infusion pumps in general and in particular to user interfaces for medical infusion pumps.

BACKGROUND OF THE INVENTION

The administration of intravenous medical fluids to a patient is well known in the art. Typically, a solution such as saline, glucose or electrolyte contained in a glass or flexible container is fed into a patient's venous system through a conduit such as a polyvinyl chloride (PVC) intravenous (IV) tube which is accessed to the patient by a catheter. Many times, the fluid is infused under the forces of gravity, and the rate of flow is controlled by a roller clamp which is adjusted to restrict the flow lumen of the IV tube until the desired flow rate is obtained.

Flow from the container to the patient also is known to be regulated by means other than a roller clamp. It is becoming more and more common to use an electronically controlled infusion pump. Such pumps include, for example, peristaltic-type pumps and valve-type pumps. Peristaltic-type pumps typically include an array of cams angularly spaced from each other which drive cam followers connected to pressure fingers. These elements cooperate to impart a linear wave motion on the pressure fingers. This linear wave motion is used to apply force to the IV tube, which imparts the motion to the fluid in the IV tube thereby propelling the fluid. An alternative type of peristaltic pump employs a plurality of roller members which roll over the IV tube to impart the motion to the fluid in the IV tube. Infusion pumps also employ pumping chambers having upstream and downstream valves to sequentially impart the propulsion to the fluid. Such valve-type pumps typically require the use of a specialized pumping cassette chamber, which is contained on a dedicated IV tube between the patient and the source of fluid.

Infusion pumps of the prior art are typically designed for a particular clinical application. For example, many pumps are designed principally for use as general floor pumps in hospital facilities. Other pumps are designed particularly for pediatric use. Other pumps are designed for critical care use. Still other pumps are principally designed for home care use. This specialized pumping use requires hospitals and health care facilities to employ a large inventory of such devices, which increases the capital investment and cost of such hospital care.

Further, it is often required that a single patient be simultaneously infused with a number of medical fluids. Most pumps employ a single flow channel, which adds to the expense and crowds the space surrounding a patient when such multiple infusions are required. Although pumps exist which employ dual channels, use of such pumps when only a single intravenous fluid is required to be infused in the patient results in unused capacity and the inability to transfer such unused capacity to other patients.

What is needed is a medical infusion pump which is readily adaptable to use in multiple clinical settings without unduly burdening the user with programming parameters for such a variety of uses. It would be further advantageous for a pump to allow the user to select the number of flow channels available or to allow for existing pumps to add flow channels as needed.

SUMMARY OF THE INVENTION

The present invention provides a medical infusion pump which is readily adaptable to use in multiple clinical settings without unduly burdening the user with programming parameters for such a variety of uses. The present invention provides a pump which allows the user to select the number of flow channels available or to allow for existing pumps to add flow channels as needed.

The present invention provides an infusion pump having a main body portion. The main body portion includes a display area for displaying user interface information. At least one pump module is provided which is removably secured to the main body portion and adapted to receive an IV tube. The pump module includes means for applying pumping action to the IV tube. The pump module further includes an auxiliary display area for displaying supplemental user interface information. A microprocessor is contained in the main body portion for generating user interface information on the display areas.

BRIEF DESCRIPTION OF THE DRAWINGS

FIG. 7 is a user interface navigation flow diagram constructed in accordance with the principles of the present invention.

DETAILED DESCRIPTION OF A PREFERRED EMBODIMENT

Figure 1:
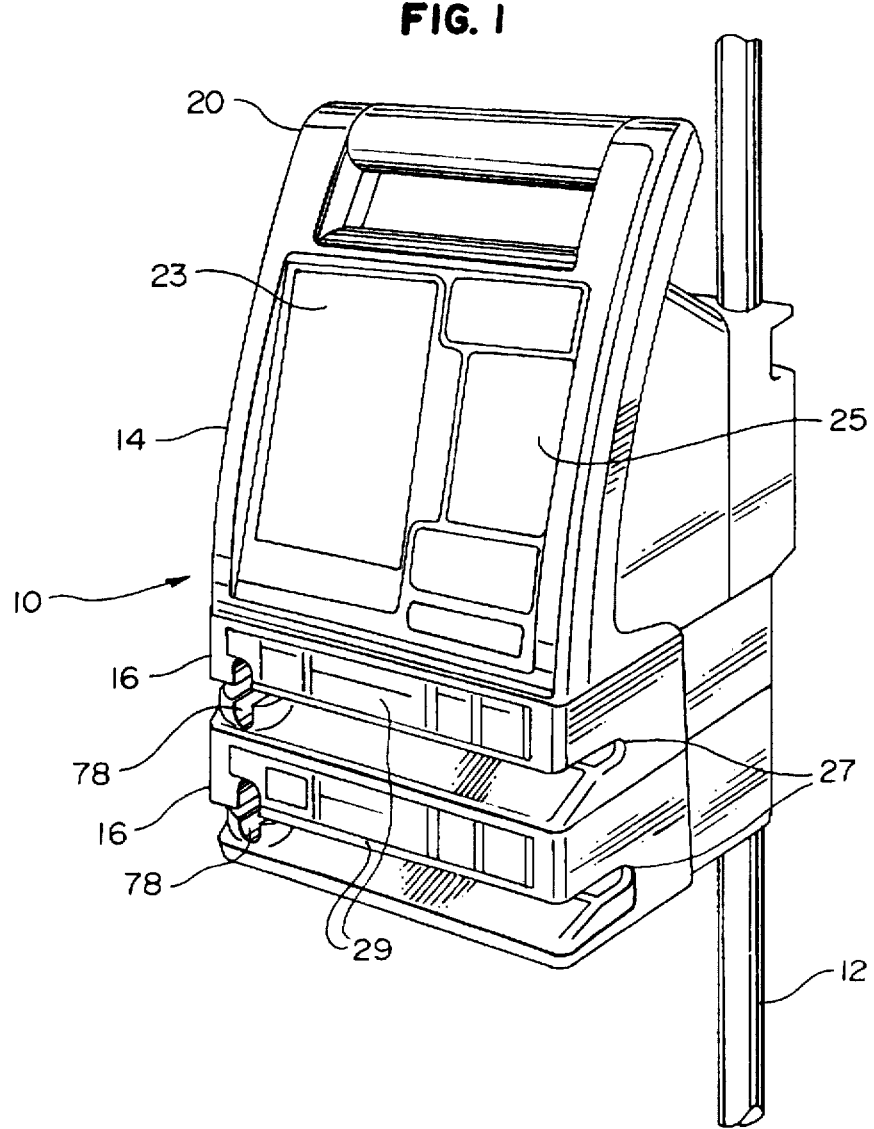
FIG. 1 is a perspective view of an infusion pump constructed in accordance with the principles of the present invention.
Figure 2:
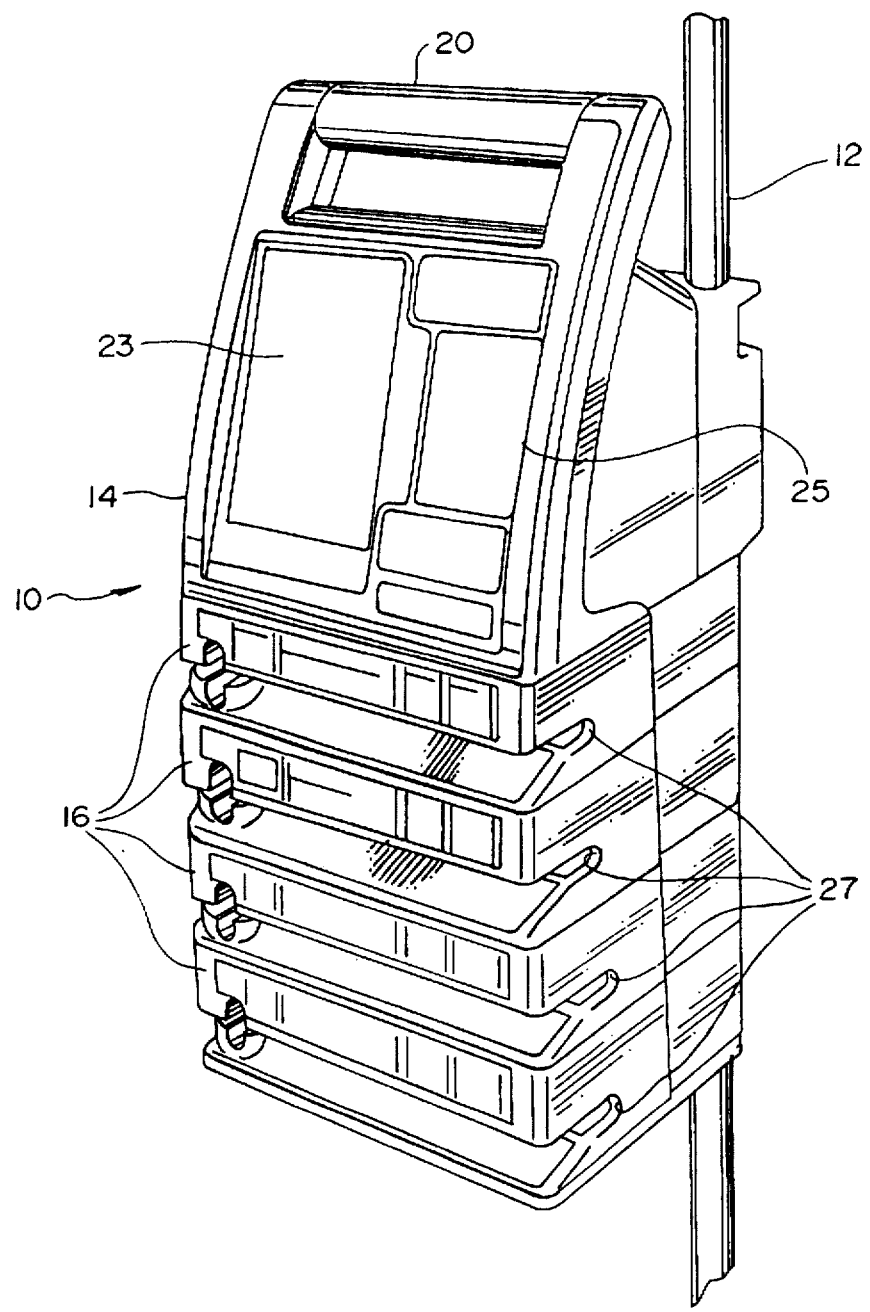
FIG. 2 is a perspective view of an alternative embodiment of an infusion pump constructed in accordance with the principles of the present invention.

Referring to FIG. 1, an intravenous fluid infusion pump made in accordance with the principles of the present invention is referred to generally as 10. The pump is clamped onto a standard IV pole 12. The pump 10 includes a main body portion 14 and at least one pump module portion 16. In the embodiment depicted and described herein, two pump module portions 16 are provided. However, the present invention contemplates the use of and provides the flexibility to use any number of pumping modules depending on the requirements of the pump user. For example, FIG. 2 shows a pump made in accordance with the principles of the present invention having four pumping modules 16.

Formed at the upper periphery of the main body portion 14 is a carrying handle 20. The main body 14 further includes a liquid crystal display (LCD) area 23 which is used to convey various information about the pump 10 to the user and provides for user interface with the pump 10, as described in more detail below. The main body 14 includes data-entry keys 25, the use of which are described in detail below. The pump module 16 includes a tube-loading channel 27 and an vacuum fluorescent display area 29, also described in detailed below. The main body portion 14 includes a slave microprocessor which is a slave to a master microprocessor. The slave microprocessor further includes an analog-to-digital converter (A/D converter). In a preferred embodiment, the master microprocessor is a 80C186 EB available from Intel Corporation, Santa Clara, Calif., and the slave microprocessor is a 80C552 available from Phillips Semiconductors, Sunnyvale, Calif. All microprocessors include software in read-only memory (ROM) which drives the user interaction and pump-monitoring functions described below.

Figure 3:
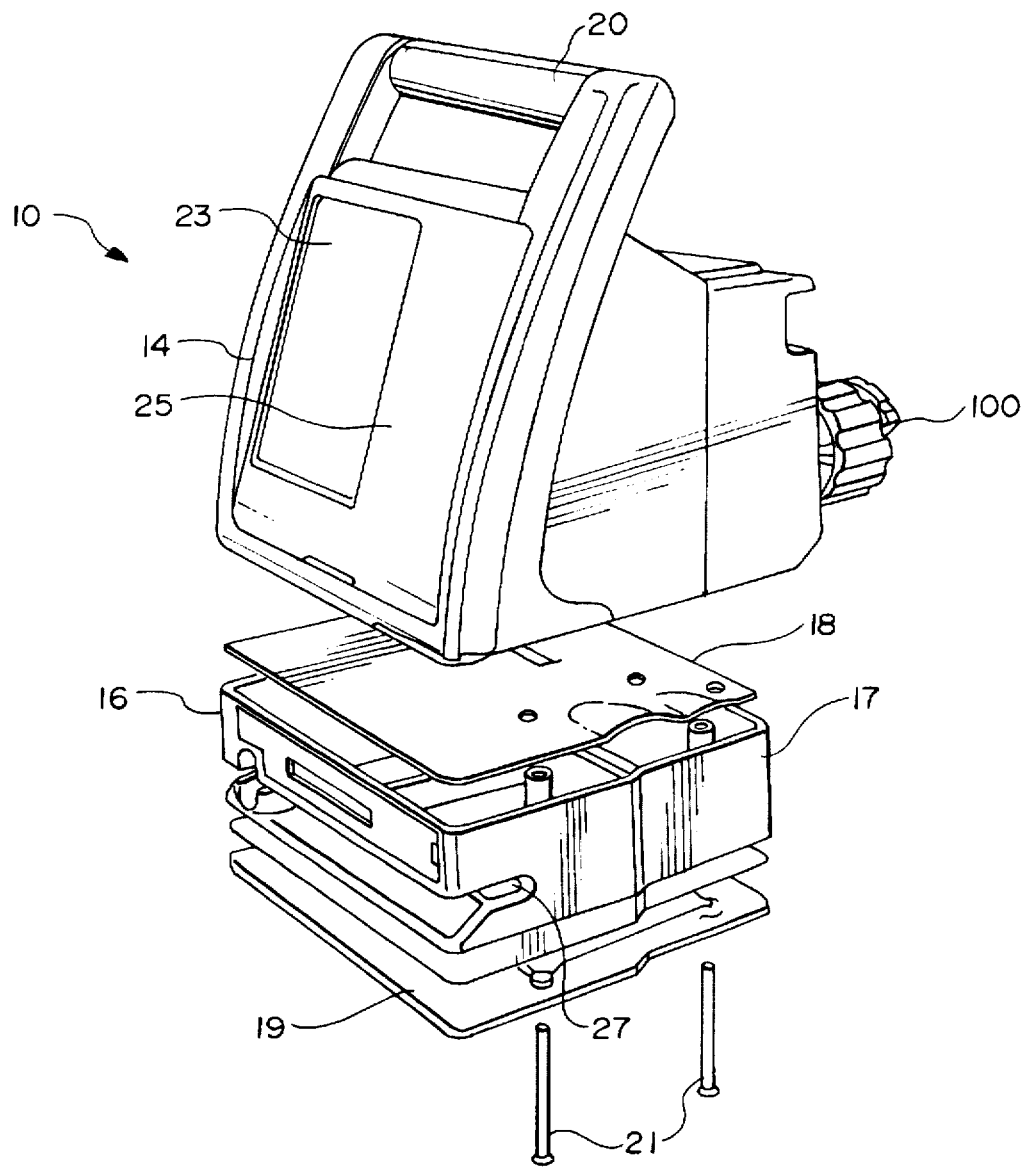
FIG. 3 is an exploded view of an alternative embodiment of an infusion pump constructed in accordance with the principles of the present invention.

It is a particular advantage that the present invention provides the flexibility to allow a user to choose a plurality of flow channels depending on the user's requirements. The present invention further allows for infusion pumps to be easily modified so that the number of flow channels can be changed. Referring now to FIG. 3, an infusion pump made in accordance with the principles of the present invention is seen in which a single module is shown in an exploded view, thus depicting the ease by which the pump module is connected to or disconnected from the main body portion.

The pump module 16 includes module housing 17, an upper module plate 18 and a lower module plate 19. Fastening means are provided to secure the pump module 16 to the main body 14. The fastening means include a plurality of extended bolts 21 which extend through apertures defined in the lower module plate 19, the module housing 17 and the upper module plate 18 to threaded apertures defined (not shown) on the bottom of the main body 14. Any number of pump modules 16 can be added to the infusion pump by utilizing the appropriate fastening means. The pump module includes a microprocessor. In a preferred embodiment, the pump module microprocessor is a 68HC11 available from Motorola, Schaumburg, Ill.

Figure 4:
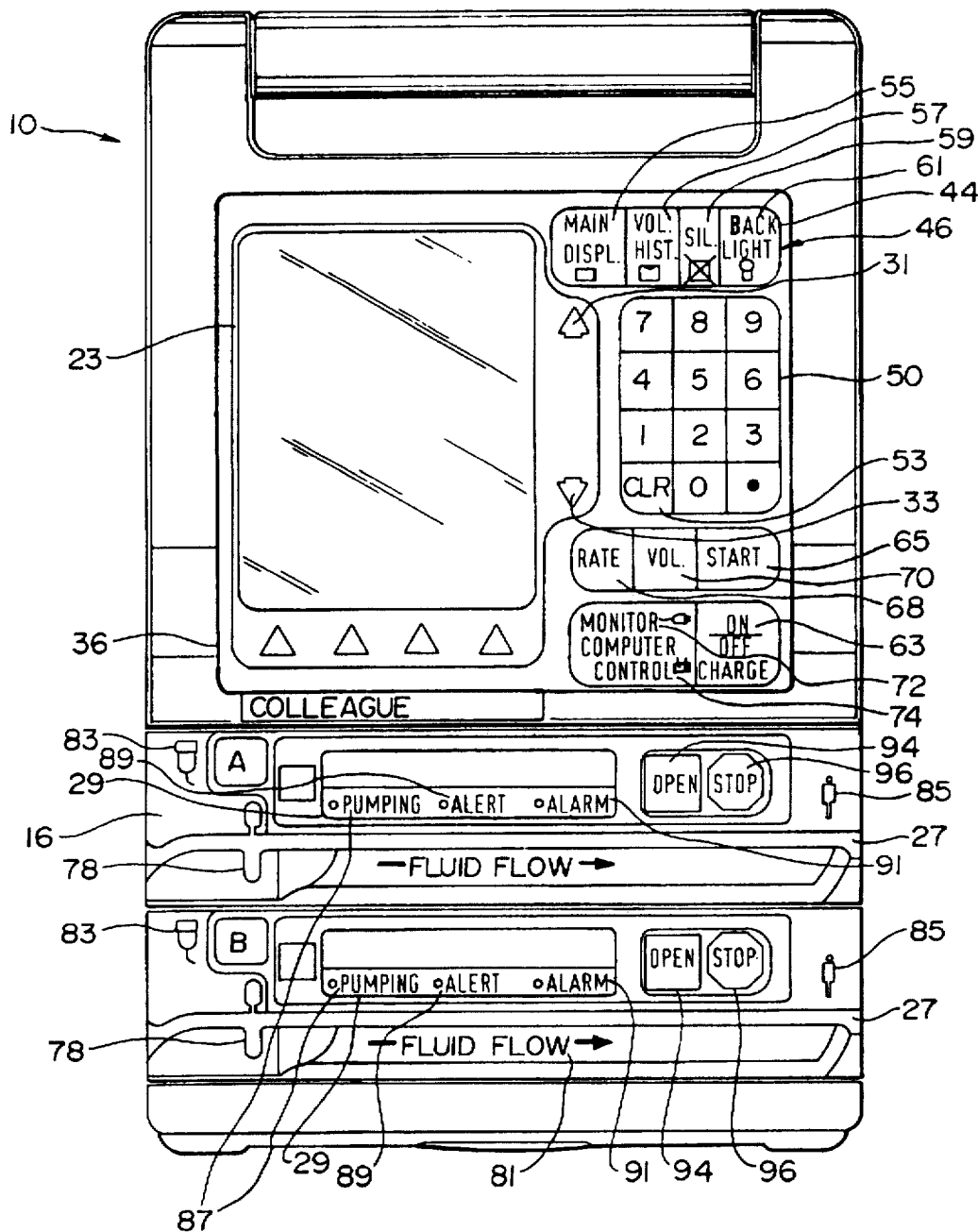
FIG. 4 is an elevational view of the infusion pump of FIG. 1, showing the detail of the pump face.

Referring to FIG. 4, an elevational view showing the detail of the face of a pump 10 made in accordance with the principles of the present invention is seen. Contained along the side of the display area 23 are a scroll-up arrow key 31 and a scroll-down arrow key 33. These keys are used to select programming fields or actions within the display area. Contained beneath the display area 23 are a plurality of arrow keys 36 which are used to interact with selection alternatives in the display area 23. Because these arrow keys 36 are used in conjunction with the particular function displayed in the display area 23, as described in detail below, these arrow keys 36 are referred to as "soft keys."

Figure 5:
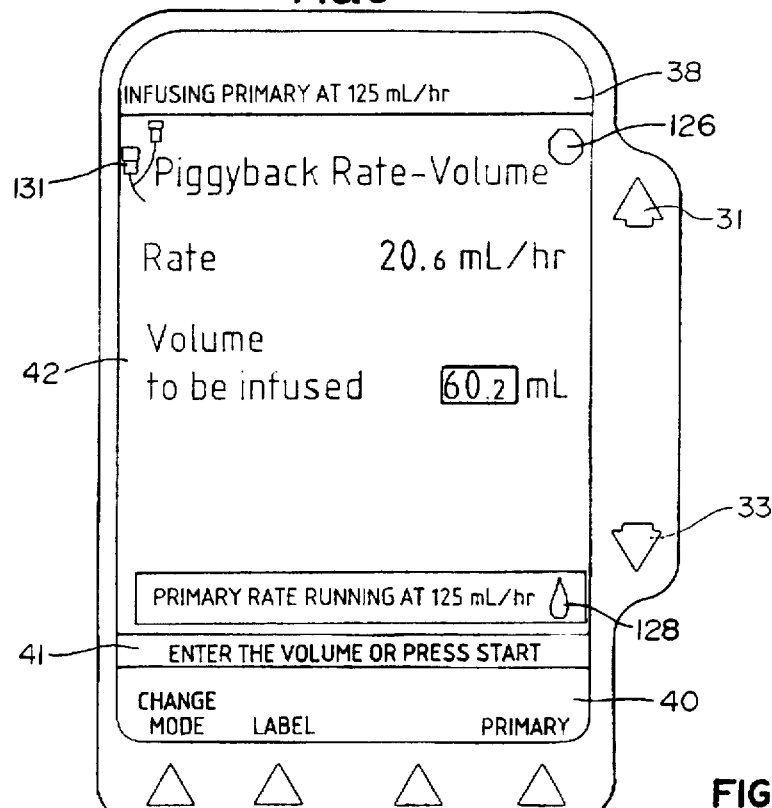
FIG. 5 is a detailed view of the display area of the infusion pumps of FIGS. 1 and 2.

Referring now to FIG. 5, an example of the display area 23 of the infusion pump is seen. The display area 23 includes four display portions. Located at the top portion of the display area is the status display 38. The status display 38 gives the status of the pump infusion. The status display 38 also identifies alert, alarm, and failure conditions. Contained at the lower portion of the display area is the prompt display. The prompt display includes a prompt line 41 which provides prompts or instructions for the user. A soft key area 40 is further provided which contains labels for the plurality of soft keys 36 located beneath the display area 23. Thus, by following the prompts and making selections in accordance with the labels applied to the soft keys 36, the user can interface with the display area 23. Finally, the middle portion 42 of the display area 23 is used for making infusion selections, programming, and displaying operating or running conditions of the pump infusion.

Referring back to FIG. 4, the main body 14 further includes a plurality of function keys 44. The function keys 44 include dedicated keys 46 which include user interface keys as well as a numeric key pad 50. Included in the numeric key pad 50 are the numbers zero through nine, and a decimal point key. These numeric and decimal point keys are used to enter programming values into the highlighted field in the display area 23, an example of which is seen in FIG. 5. The numeric key pad 50 further includes a clear key 53 which is used to clear values from the highlighted field. As a safety feature against inadvertent clearing of values from the highlighted field, if the clear key 53 is again pressed after the highlighted field has been cleared, the content of the field is restored to the last value stored in the master microprocessor's memory.

The dedicated function keys 46 include a main-display function key 55. The maindisplay function key 55 is used to return the display area 23 to the main display from any point in the user interaction. The volume-history function key 57 is used to display the volume history screen. The silence function key 59 silences pump alarms and pump alerts for a predetermined period, such as two minutes in the preferred embodiment. The back-light function key 61 serves one purpose when the pump is plugged into an electrical outlet, and a related but second purpose when the pump is on auxiliary battery power. When plugged into an electrical outlet, the back-light function key 61 turns the display back lights on and off. When on auxiliary battery power, the back-light function key 61 illuminates the display back lights, but in order to conserve power the back lights do not remain on indefinitely.

Included in the action keys is an on/off charge key 63. The on/off charge key 63 powers the infusion pump 10 on and off. When the pump 10 is infusing, pressing the on/off charge key 63 will provide a system override to stop the infusion. The action keys further include a start key 65. If all of the required programming values have been collectibly entered during the programming mode, the start key 65 initiates the infusion. Following an alarm notification, once the alarm condition is resolved the start key 65 cancels the alarm notification and restarts the infusion. The action keys further include a rate key 68, which is used to select the rate values, and a volume key 70, which is used to select the volume parameters.

Two additional icons are used as indicators of pump conditions. The electronic-plug icon 72 indicates when the infusion pump 10 is plugged into an electrical outlet. The electronicplug icon 72 also indicates that the auxiliary battery is being charged from the electrical power provided by the electrical outlet. A battery icon 74 is further provided, which is lit when the pump 10 is operating on auxiliary battery power. In an additional embodiment, two additional icons are used. A computer control icon indicates when an external computer is transferring data to the pump and a monitor icon indicates when an external computer is querying information from the pump.

At least one pump module 16 is located beneath the main body 14 of the pump 10. While the pump modules depicted in the preferred embodiment described herein are standard IV tube pump modules, the present invention contemplates use of alternative pump modules employing alternative pumping technology, such as for example, syringe pump modules. The pump module 16 includes a tube-loading channel 27 into which a standard IV tube is loaded into the pump 10. The pump module 16 includes an automatic tube-loading feature. Contained within the tube-loading channel 27 is a keyed slot 78 adapted to receive a slide clamp contained on the IV tube. The pump module 16 includes a free-flow prevention feature.

In order to assure that the IV tube is loaded into the pump module 16 in the proper orientation, the pump module 16 contains several safety features. Initially, the slide clamp 80 is keyed such that it only fits into the keyed slot 78 in the proper orientation. Additionally, beneath the tube-loading channel 27, a fluid flow arrow 81 is provided to instruct the user as to the proper direction of fluid flow in the IV tube. Still further, on the left side of the pump module 16 an intravenous solution bag icon 83 is provided. This reminds the user that the end of the IV tube that connects to the solution bag is to be directed to the left side of the tube-loading channel 27. Still further, on the right side of the pump module 16 is a patient icon 85. This icon 85 is used to remind the user that the end of the IV tube that connects to the patient is to be directed to the right side of the tube-loading channel 27.

The pump module vacuum fluorescence display area 29 further includes a character display area. In the preferred embodiment depicted herein, an eight-character display area is provided. The display area is used to prompt or instruct the user during specific pump interaction operations. The display also is used during an alarm or alert condition to identify the particular condition. Finally, the display is used during infusion to provide an indication of the status of the infusion.

Contained beneath the character display area are three light-emitting diode (LED) status indicators. The first is a green LED 87 which indicates when the pump is infusing. The second is a yellow LED 89 which indicates when the pump is in an alert condition. The yellow LED 89 remains continuously lit during an alert condition, provided there are no active alarms. The third is a red LED 91 which indicates when the pump is in an alarm condition. The red LED 91 flashes on and off during an alarm condition and remains lit continuously during a failure condition. If the infusion pump 10 is running on auxiliary battery power, the alert or alarm display will flash on and off in order to conserve battery power.

The pump module 16 also includes an open-action key 94 and a stop-action key 96. The open-action key 94 opens the loading mechanism so that an IV tube can be loaded into the tubeloading channel 27. When an IV tube is contained in the pump module 16, the open-action key 94 opens the loading mechanism to allow removal of the IV tube. The stop-action key 96 provides a system override to stop any active infusion.

Figure 6:
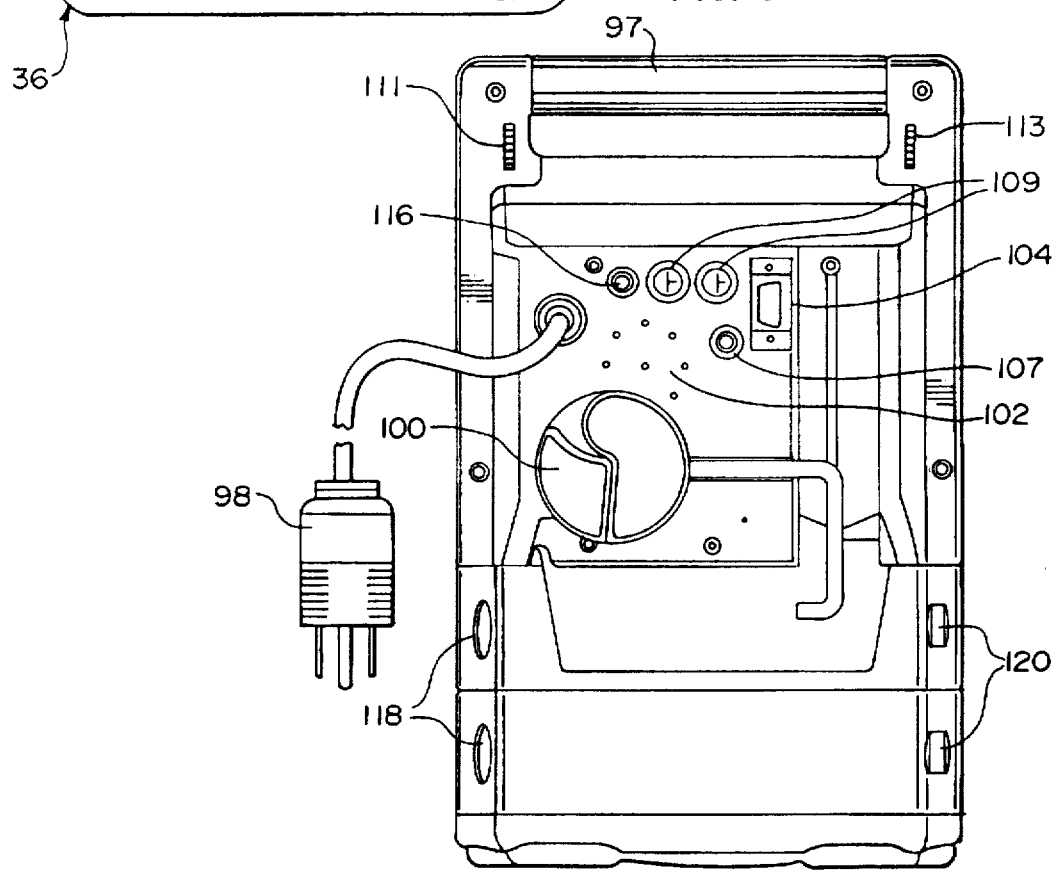
FIG. 6 is an elevational view of the rear of the infusion pump of FIG. 1.

Referring now to FIG. 6, the rear 97 of the infusion pump 10 is seen. The infusion pump 10 includes a grounded power cord 98 for plugging the pump into a wall outlet to provide standard alternating current (AC) to power the infusion pump 10 and to recharge the auxiliary battery. The device further includes a mounting clamp 100 which is used to mount the pump 10 onto an IV pole. An audio speaker grill 102 is provided over an audio speaker which is used to generate alert and alarm condition and audio tones when keys are pressed. A communications port 104 is provided to allow the pump 10 to connect and communicate with a computer. The communications port 104 also can be used to communicate the nurse call signal to a computer located at a nurse station. In the preferred embodiment, an RS 232 compatible interface is provided for external communications.

A direct current (DC) receptacle 107 is further provided. The DC receptacle 107 enables the pump 10 to be connected to external DC power sources, such as for example, the 12-volt power source provided in most U.S. vehicles, to enable the pump 10 to be used with an ambulatory patient. The rear 97 of the infusion pump 10 further includes fuse compartments 109 which contain electronic fuses as known in the art, an audio speaker volume control 111, and a contrast adjustment 113 for the main display. Further provided is a panel lock button 116. Enabling the panel lock button 116 disables many of the front panel keys to prevent inadvertent reprogramming as well as deliberate tampering with the pump.

Contained on the side of each pump module is a manual-tube release knob 118. This knob 118 provides a manual override of the automatic tube-loading and unloading feature in the pump module 16. This allows the user to manually release the tubing from the pump 10. Further provided on each pump module is a drop-sensor port 120. This port 120 allows for connection to the pump 10 of an optional drop sensor, which is used in conjunction with a standard drip chamber.

Referring now to FIG. 7, a user interface navigation flow diagram is seen. The figure depicts an overview of the user interface routine discussed in detail below. Upon power-up, the infusion pump performs diagnostic tests while the self-diagnostic routine 300 occurs. After completion of the diagnostic tests, a power-on screen is displayed. From the power-on routine 302, the user can access the main display routine 304 or a select set of configuration parameters routine 306. If the select set of configuration parameters routine 306 is selected, the user can access a series of view set of configuration parameters subroutines 308. From the select set of configuration parameters routine 306 or the view set of configuration parameters subroutines 308, the main display routine 304 can be accessed. From the main display routine 304, the user can access a plurality of routines. An options menu routine 311 provides access to the view set of configuration parameters series of subroutines 308, a change occlusion settings routine 313, a battery display routine 315 and a configuration/service routine 317. From the options menu routine 311, the series of view set of configuration parameters subroutines 308, the change occlusion settings routine 313 and the battery display routine 315, the main display routine 304 and a configuration/service routine 317 can be accessed.

The configuration/service routine 317 includes a password entry subroutine which limits access to authorized hospital personnel having a password. Upon input of an authorized password, the authorized hospital personnel can access a configuration/service menu subroutine 319. The configuration/service menu subroutine 319 provides access to a device configuration utility subroutine 322, an event history subroutine 324, a service features subroutine 326, and a transfer device configuration subroutine 328. From the device configuration utility subroutine 322, the authorized hospital personnel can access a copy set of configuration parameters subroutine 331 and a series of edit set of configuration parameters subroutines 333. From the service features subroutine 326, the authorized hospital personnel can access a series of service subroutines 335. From the configuration service menu routine 319, the power-on routine 302 can be accessed.

Further programming routines can be accessed from the main display routine 304. These further programming routines include a primary rate-volume programming routine 339, a primary volume-time programming routine 341, a series of primary dose programming routines 343, a primary ramp programming routine 345, a piggyback rate-volume programming routine 347 and a piggyback volume-time programming routine 349.

Each of these programming routines provides access to the change mode pop-up window subroutines 352 which provide the ability to switch to other programming routines and to the main display routine. The pop-up window subroutines 352 include a prime pop-up subroutine 354 and a standby pop-up subroutine 356. The prime pop-up subroutine 354 and the standby pop-up subroutine 356 provide access to the main display routine 304. The prime pop-up subroutine 354 can be accessed from each of the programming routines. A volume history routine 358 is available from most of the routines.

Referring now to FIGS. 8 to 30, the user interaction with the infusion pump 10 is described in detail. As previously discussed, the user interaction is principally conducted through the main display area 23, including the scroll-up and scroll-down arrow keys 31, 33 contained on the side and the soft keys 36 displayed underneath the display area.

Upon power-up of the pump 10 by pressing the on/off charge key 63, the pump selfdiagnostic tests begin. The main display area 23 initially is lit, then goes dark, while the pump module display 29 illuminates each of the character positions. Next, the LEDs are lit and the audible speaker is activated, followed by the sounding of the back-up beeper. This procedure enables the user to check for dark spots or lines on the display when the screen is lit, check for light spots or lines on the display when the screen is dark, ensure that the pump module display characters are appropriately lit, ensure that all of the LEDs are in working order, and hear that the audible speaker and back-up buzzer tone are active.

Figure 8A:
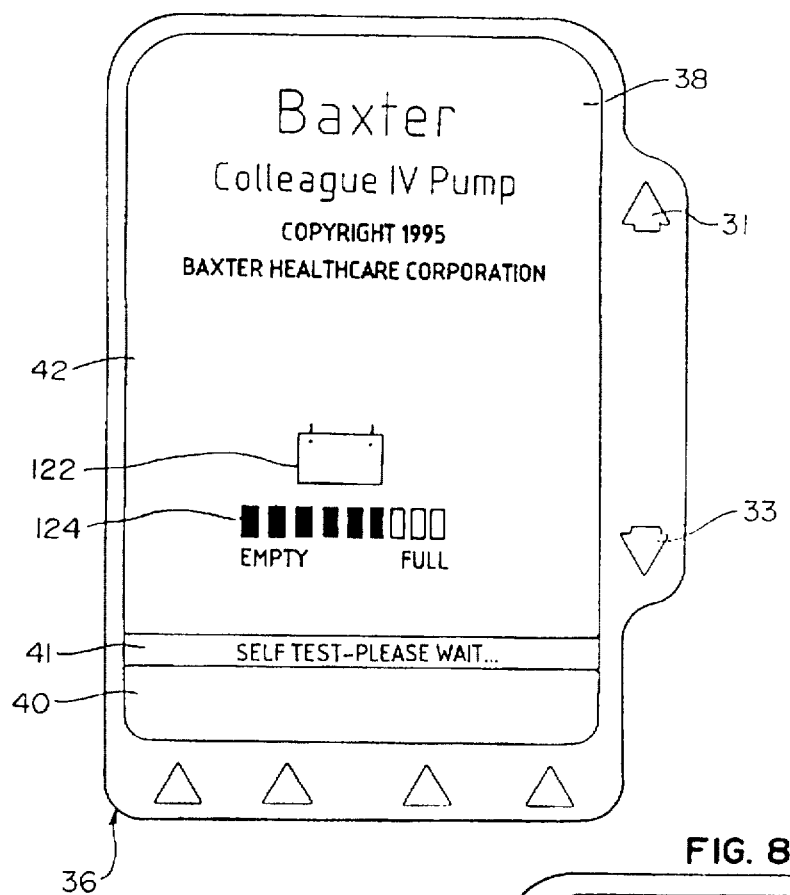
FIGS. 8 to 30 shows the details of the user interaction with a pump constructed in accordance with the principles of the present invention.

Once the display area, LED, and speaker tests are complete, the screen displays the pump identification screen seen in FIG. 8(a). This screen includes a battery icon 122. The battery icon 122 includes a gauge 124 which graphically demonstrates the amount of amp hours remaining in the rechargeable auxiliary battery. In this initial screen, the prompt line 41 identifies that the pump self-diagnostic tests are proceeding and instructs the user to wait until the self-diagnostic tests are over.

Figure 8B:
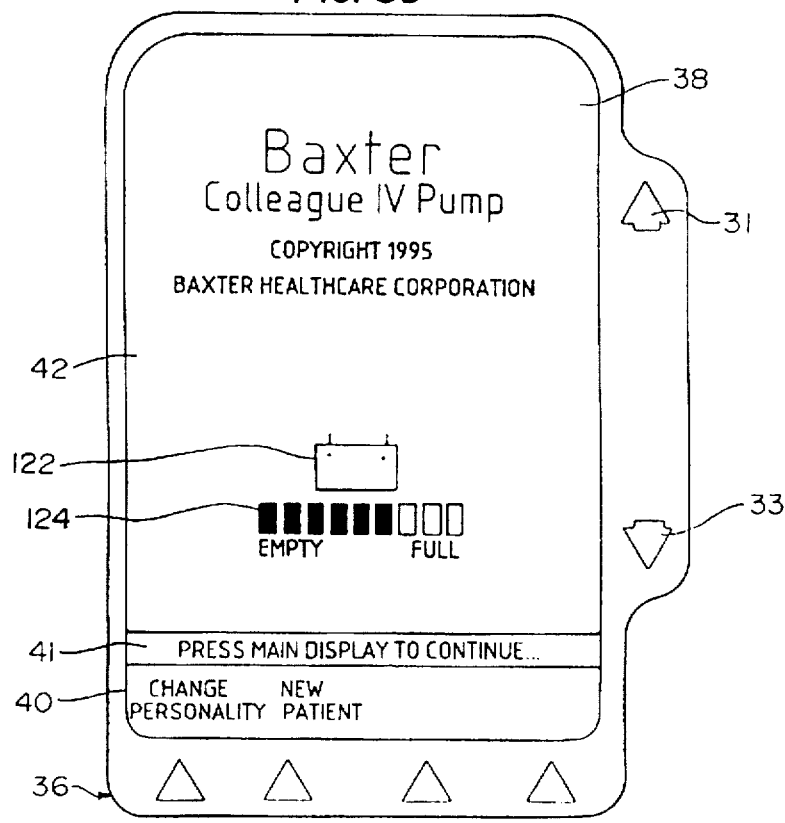

Referring now to FIG. 8(b), after the self-diagnostic tests are completed, the prompt line 41 instructs the user that the pump 10 is ready to continue into the programming mode. Additionally, several soft keys are made available, depending on the configuration options chosen by the user. For example, in the embodiment depicted in FIG. 8(b), a soft key labeled "change Personality"™ is present which enables the user to enter a mode to change the previously selected set of configuration parameters, as described in more detail below. Additionally, a soft key labeled "new patient" is present, indicating that information from a previous program is still retained in the memory. Pressing the "new patient" soft key will clear the programming memory and volume history from this previous patient. As instructed in the prompt line 41, pressing the main display key 55 advances the display area to the main display screen.

Figure 9A:
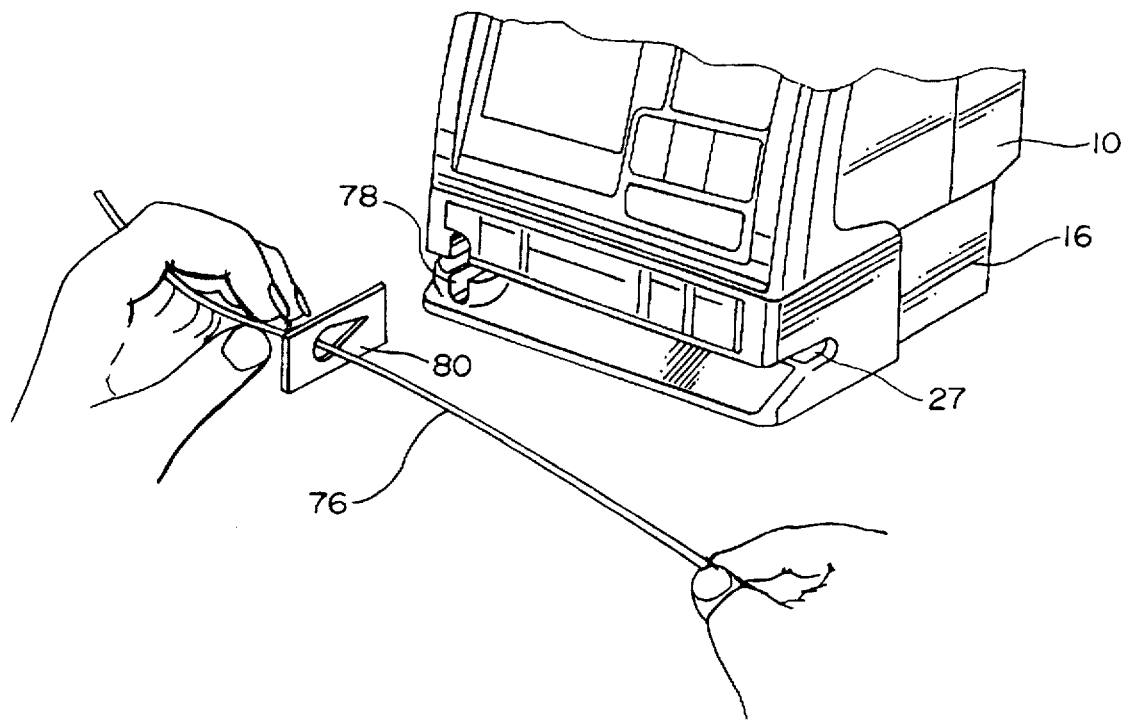
Figure 9B:
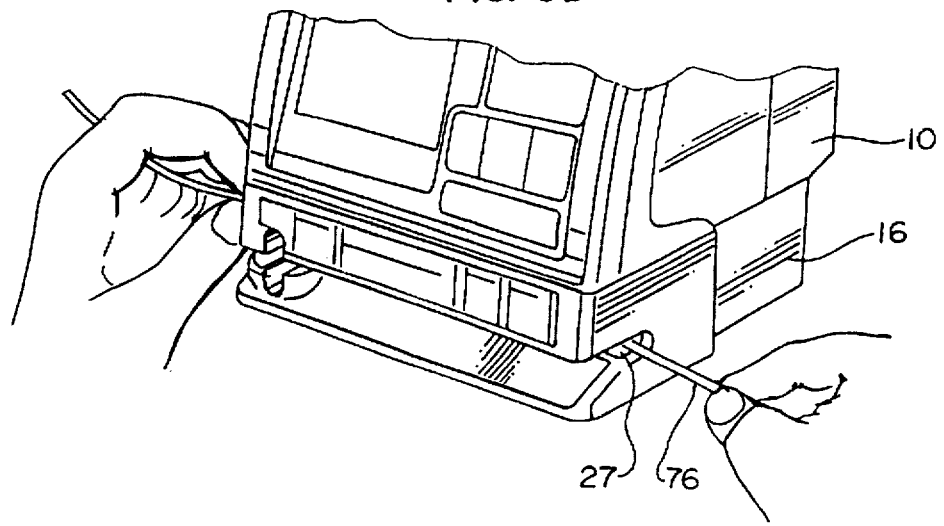

Prior to programming the infusion pump 10, the user is instructed to load an IV tube into the pump module 16. Referring to FIG. 9, the loading of the IV tube into the automated tubeloading slot in the pump module 16 is described. Initially, the open key 94 is pressed, which causes the automatic tube-loading mechanism to open. As seen in FIG. 9(a), the user positions the on/off slide clamp 80 into the keyed slot 78, which helps assure the proper orientation of the IV tube. Pulling the IV tube taut, as seen in FIG. 9(b), the user slides the IV tube into and along the tube-loading channel 27. Once the pump 10 detects the presence of the IV tube, the pump 10 automatically loads the IV tube into the proper position in the pump drive mechanism. If the IV tube is not loaded in a given predetermined time period, 30 seconds in the preferred embodiment, after the open key 94 has been pressed, the automatic tube-loading mechanism will close to assure that an inadvertent loading of an improper IV tube does not occur. Additionally, when off, pressing the open key 94 powers on the infusion pump 10 so that the IV tube can be loaded into the device.

Figure 8C:
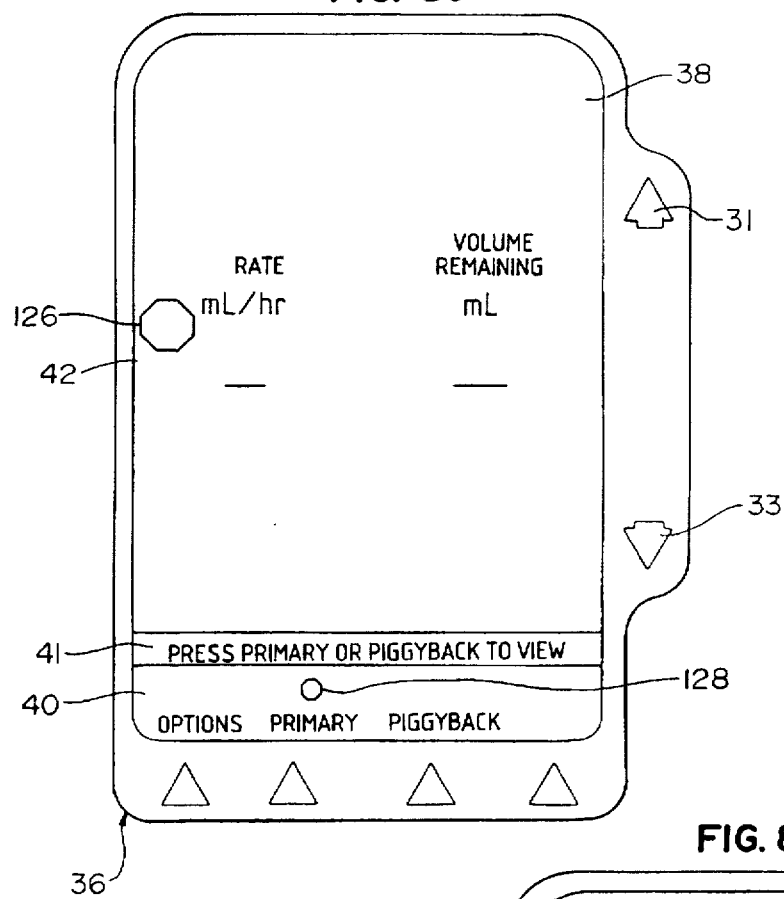

After loading the IV tube, the main display screen returns to the display area, as depicted in FIG. 8(c). The main display screen includes the stop icon 126 which indicates that the pump 10 is not infusing. The soft keys 36 include an "option" key, a "primary" key, and a "piggyback" key. A stop icon 128 contained above the "primary" soft key indicates the default infusion. The display screen prompt instructs the user to press the "primary" soft key or "piggyback" soft key to view the programming mode for those two infusions.

Figure 8D:
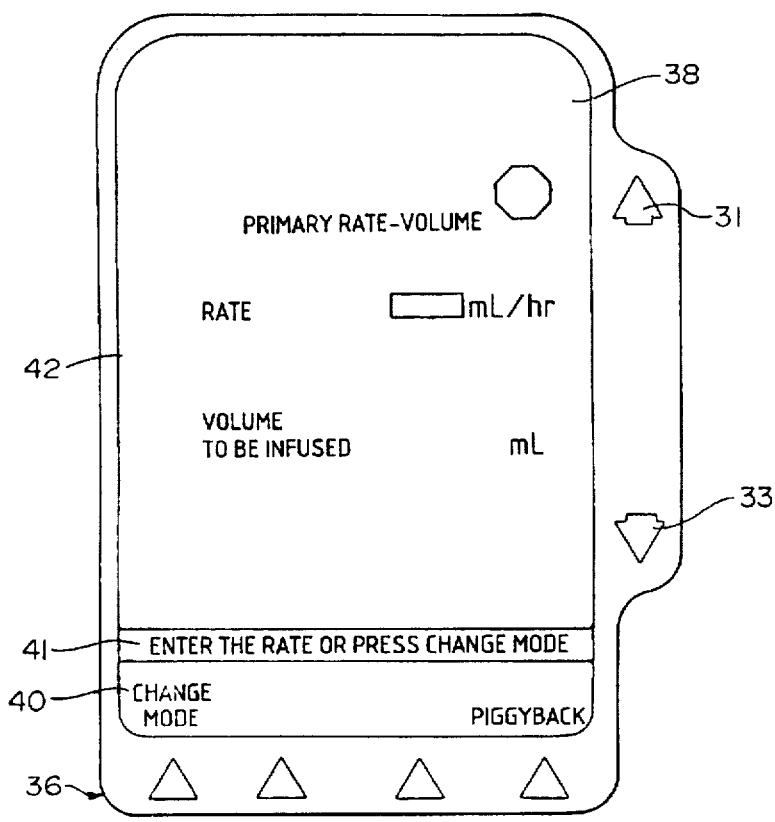

To begin programming the infusion pump 10, the rate key 68 is pressed, which changes the display to the rate-volume programming screen with the rate field highlighted, as seen in FIG. 8(d). If neither the "primary" soft key nor the "piggyback" soft key is pressed, the programming mode assumes the default infusion is to be programmed. The rate-volume programming screen prompt line instructs the user to enter the rate or press change mode, while the soft key options include the "change mode" key, the "piggyback" key and label line. Once the desired flow rate is entered by the user into the numeric key pad 50, either the volume or the arrow key can be used to highlight the volume field. The volume to be infused can then be entered by the user using the numeric key pad. For standard primary infusion, this completes the programming steps.

During programming, if incorrect values are entered by the user, pressing the clear key 53 clears the incorrect value so that the correct value can be programmed using the numeric key pad 50. To begin the infusion, the start key 65 is pressed. If the programmed values exceed an allowable range preprogrammed into the master microprocessor based on the particular set of configuration parameters chosen by the user, an out-of-range alarm will be activated upon pressing the start key 65.

Figure 10A:
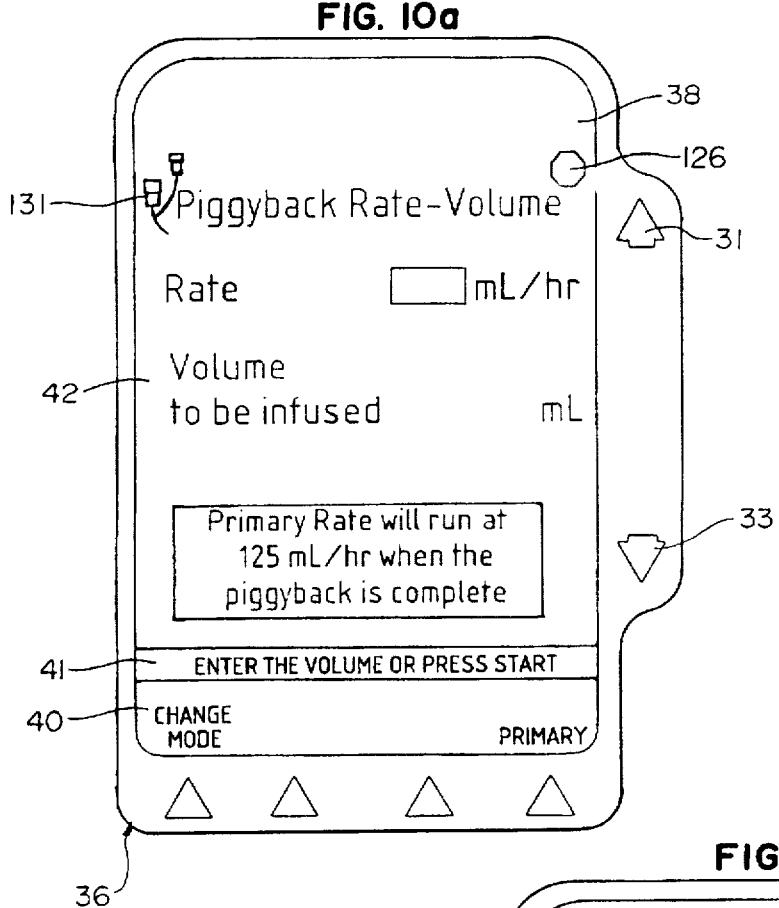

If a piggyback infusion is desired, the "piggyback" soft key is depressed. The stop icon 128 over the piggyback rate-volume programming screen is displayed. The rate and volume to be infused in the piggyback is entered in the same manner as the rate and volume information for the primary infusion. As seen in FIG. 10(a), the piggyback rate-volume programming screen includes the piggyback icon 131, and the display area includes a message informing the user of the primary infusion information. To begin the piggyback infusion, the start key is pressed.

Figure 11A:
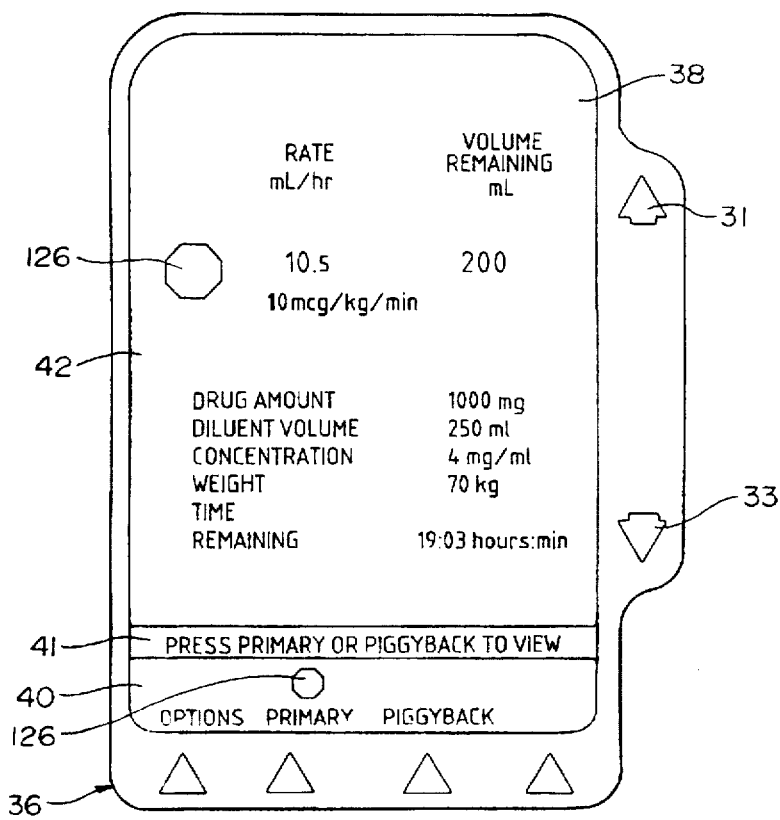
Figure 11B:
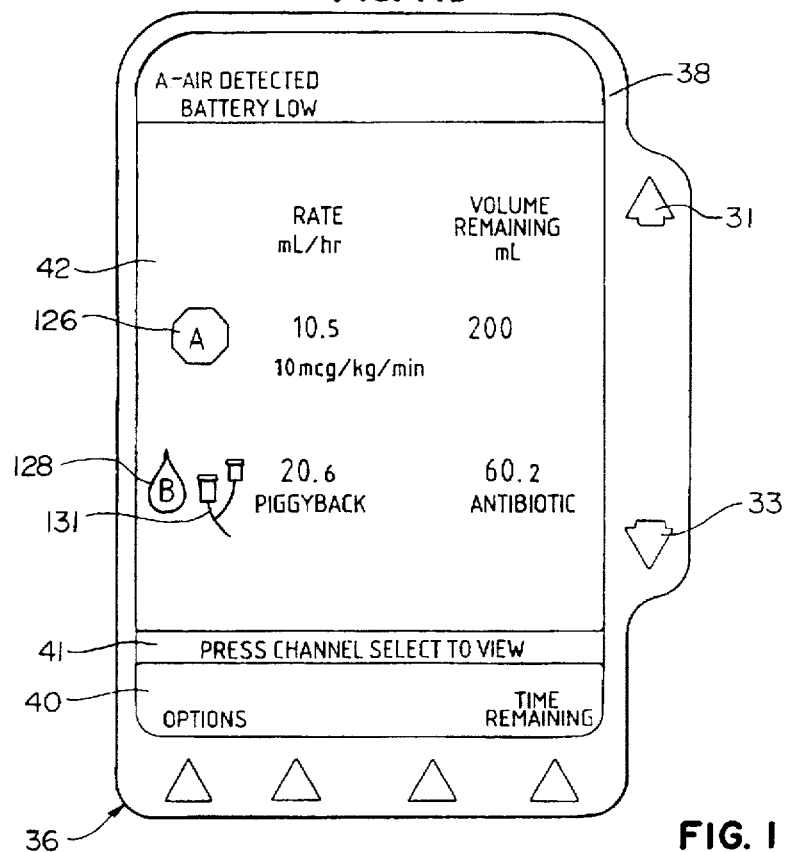

Referring to FIG. 11(a), the main display is seen for a single channel with a stopped primary infusion. The main display includes the programmed rate of infusion, the volume remaining to be infused, and the time of infusion remaining. The main display can further include programmed information about the infusion, such as the total amount of drug, the total volume of diluent, the drug concentration, the weight of the patient and ramp information. The soft keys include an "options" soft key, a "primary" soft key and a "piggyback" soft key. Pressing the "primary" soft key or the "piggyback" soft key will display the information for the respective infusion.

Figure 11C:
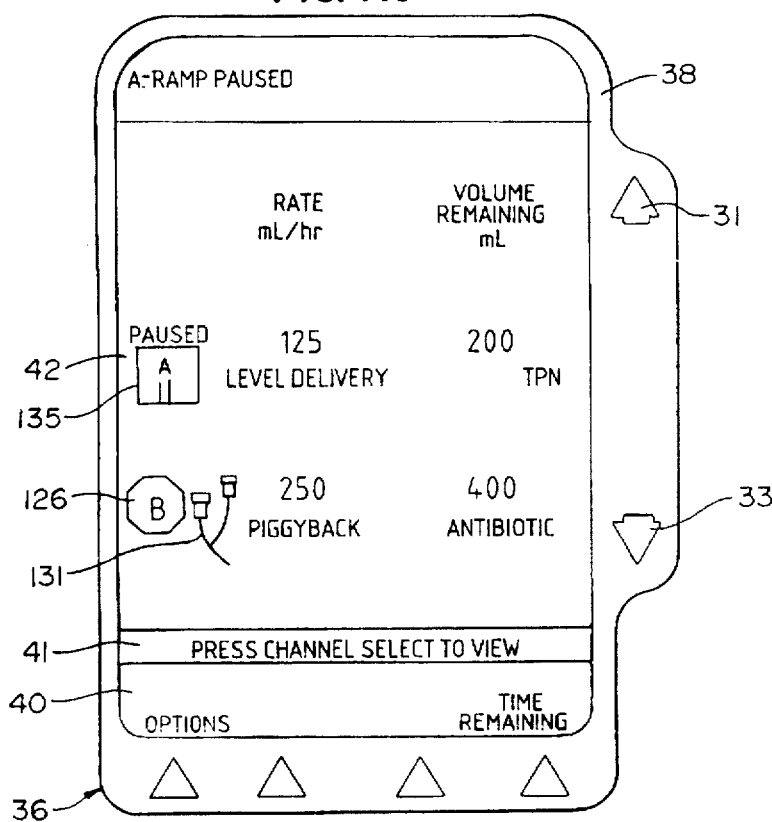

When the infusion pump is operating with a plurality of flow channels, the main display displays configuration parameters for the active channels. For example, referring to FIG. 11(b) for an infusion pump with a low auxiliary battery condition and two active flow channels, the first flow channel is designated "A" and the second flow channel is designated "B." Flow channel A is a primary infusion which has been stopped because of an air detect, while flow channel B is a labeled, infusing piggyback. All this information plus the designated flow rate and the volume remaining to be infused is depicted in the main display. Referring to FIG. 11(c), a second example is seen with a labeled, paused ramp infusion on flow channel A and a labeled, stopped piggyback on flow channel B. A pause icon 135 is displayed for flow channel A.

When infusing, the display area will show a droplet icon 128 to indicate that the pump 10 is operational. The programmed rate of delivery, the volume of fluid remaining to be delivered, and/or the time remaining to deliver the remaining volume will be displayed. To stop an infusion before it is completed, the stop key is pressed. The droplet icon 128 will be replaced with the stop icon 126 on the main display, and the pump LED will no longer be illuminated. To restart the infusion, the start key is pressed.

Figure 10B:
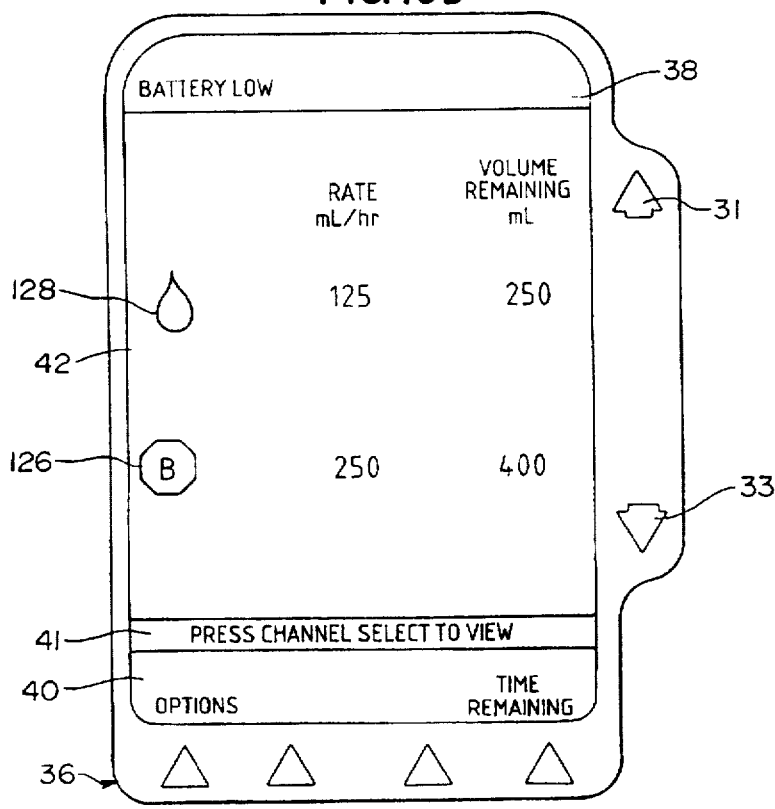
Figure 10C:
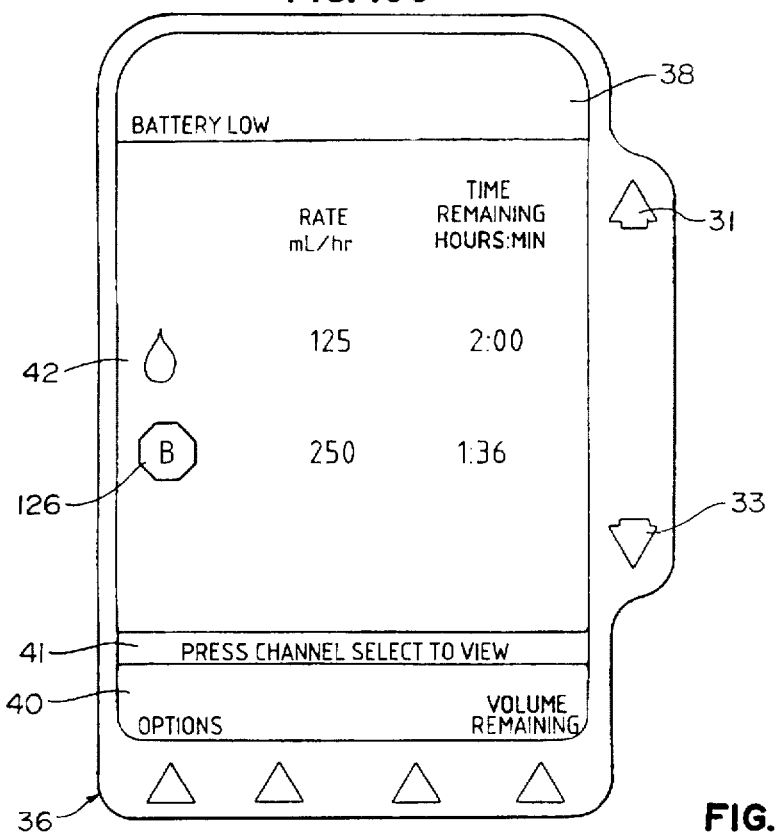

When the infusion pump is operating with a plurality of flow channels, the volume remaining and time remaining are not displayed at the same time due to space constraints. Referring to FIG. 10(b), the volume remaining is displayed for two active channels with channel A running and channel B stopped. When the volume remaining is displayed, a "time remaining" soft key is provided which displays the volume remaining. When the time remaining is displayed, as seen in FIG. 10(c), a "volume remaining" soft key is provided to toggle to that display.

If the pump is not restarted within a predetermined period of time, a channel stop alert will sound. The pump also can be stopped if any alarm condition occurs or if the on/off charge key is pressed while running. The piggyback infusion is stopped by closing the on/off clamp on the secondary infusion tube and pressing the stop key. To continue with the primary infusion, the "primary" soft key is pressed to change the operation mode of the pump, followed by the pressing of the start key to begin the primary infusion.

During infusion, information on the primary, piggyback, and accumulated volume infused by the pump since the last time the volume was cleared can be reviewed by pressing the volume history key. The volume history screen will appear on the display area, and information on the volume infused by the infusion pump, including the date and time the volume was cleared, can be viewed. The volume history is retained in the master microprocessor's memory for a predetermined period of time even if the pump is turned off. The information includes the date and time the pump volume history was last cleared, the total volume cleared at that time, and the current date and time.

Figure 12:
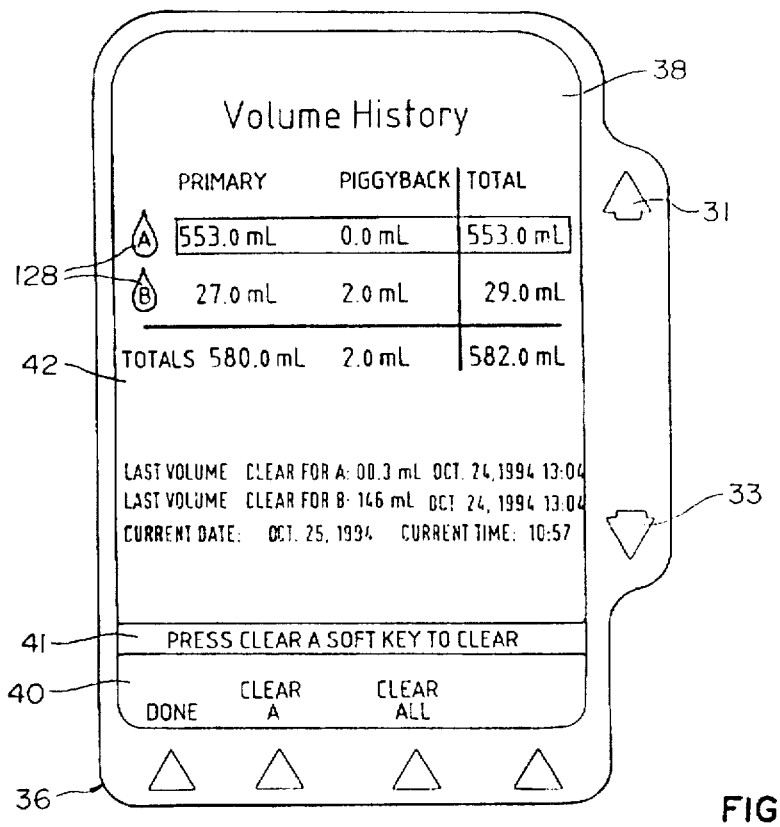

The prompt line includes instructions on how to clear the volume history. When the infusion pump is operating with a plurality of flow channels, the volume history displays the history of the active channels. FIG. 12 contains an example of volume history for an infusion pump with two active channels. A "clear" channel soft key and "done" soft key are provided. If the user desires to clear the volume history, the "clear" channel soft key is pressed. If the user desires to return to the screen from which the volume history screen was accessed, the "done" soft key is pressed. Alternatively, after a predetermined time lapses with no key selection, the pump will automatically return to the screen from which the volume history screen was accessed. If, in the power-on programming mode, the "new patient" soft key is selected or the set of configuration parameters are changed, the volume history will automatically be cleared.

The infusion pump also provides the ability to change flow rate during an infusion. To change the flow rate, the rate key is pressed. This causes the rate field in the display area to highlight. The prompt line instructs the user to enter the new flow rate, and a "rate up" soft key and a "rate down" soft key may be provided. The flow rate can be changed by pressing the "rate up" or "rate down" soft keys to increase or decrease the flow rate. Alternatively, the numeric key pad can be used to enter a new value into the rate field. After the new rate has been entered into the infusion pump, to begin infusing at the new rate, the start key is pressed.

Once the volume remaining to be infused reaches zero, indicating the infusion is concluded, the pump will automatically enter a keep-vein-open (KVO) alert mode. During this alert mode, the pump will continue infusing at the lesser of a preprogrammed KVO rate or at the programmed rate. To exit the KVO alert mode, the stop key is pressed. The infusion pump can then be programmed for the next infusion or the pump can be powered off.

After the end of the infusion, to unload the IV tube, the open key is pressed. The pump module automatically closes the slide clamp and opens the tube-loading channel to allow removal of the IV tube. Upon removal of the IV tube, the auto load mechanism will close. Alternatively, if the IV tube has not been removed after a predetermined time period, the mechanism will automatically close.

The IV tube can be removed on an infusion pump that is not powered on. If the open key is pressed while the infusion pump is off, the open key will temporarily power the unit, to allow removal of the IV tube. The display area includes a special instruction directing the user to close and remove the slide clamp and the IV tube. As an additional safety feature, a manual tube release is provided as a redundant safety feature to allow the IV tube to be unloaded if the loading mechanism becomes disabled.

The lock function disables all of the front panel keys except the main display, volume history, and back-light key, and the arrow keys as well as the "option," "primary," "piggyback," "channel select" and "select" soft keys for viewing. The lock function can only be enabled when the infusion pump is in a standby mode or during an infusion with no alarm or alert conditions present. When the lock function is enabled, the display area includes a lock icon beneath the prompt line. Alternatively, an auto-lock function can be provided which automatically locks the front panel keys after an infusion has been started if no alarms or alerts are present.

Figure 13A:
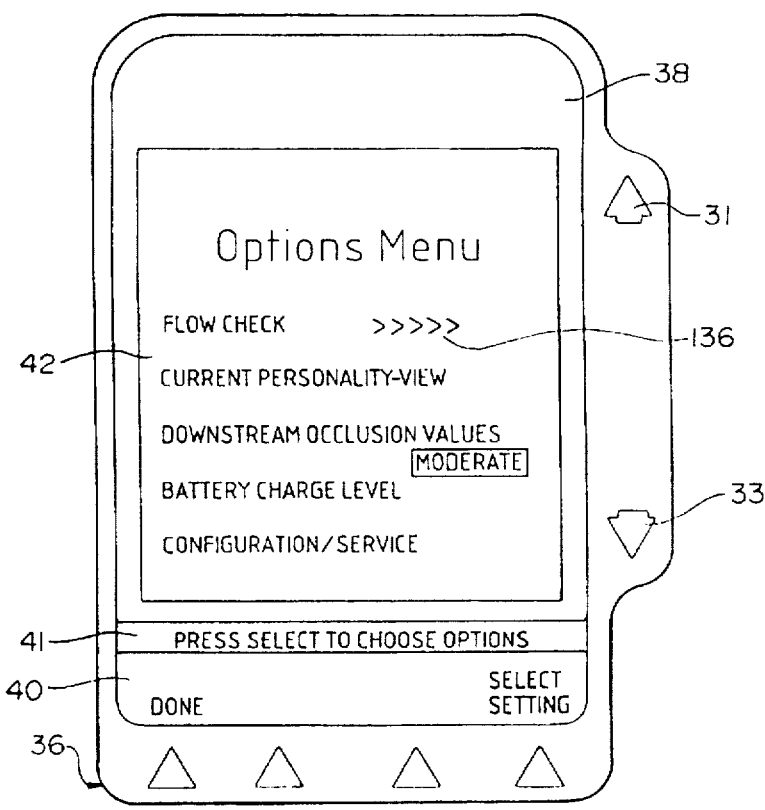

The infusion pump includes several additional user features. Referring now to FIG. 13(a), a pop-up window is seen which displays an options window if the "option" soft key is pressed from the main display. The options menu includes a flow check feature, a current Personality™ view feature, the selection of the downstream occlusion values, the battery charge level feature, and the configuration/service feature. In order to view the particular available features, the user highlights the feature to be viewed using the scroll-up and scroll-down arrow keys. The current Personality™ view feature allows a quick review of the current set of configuration parameters, as described in detail below.

Figure 13B:
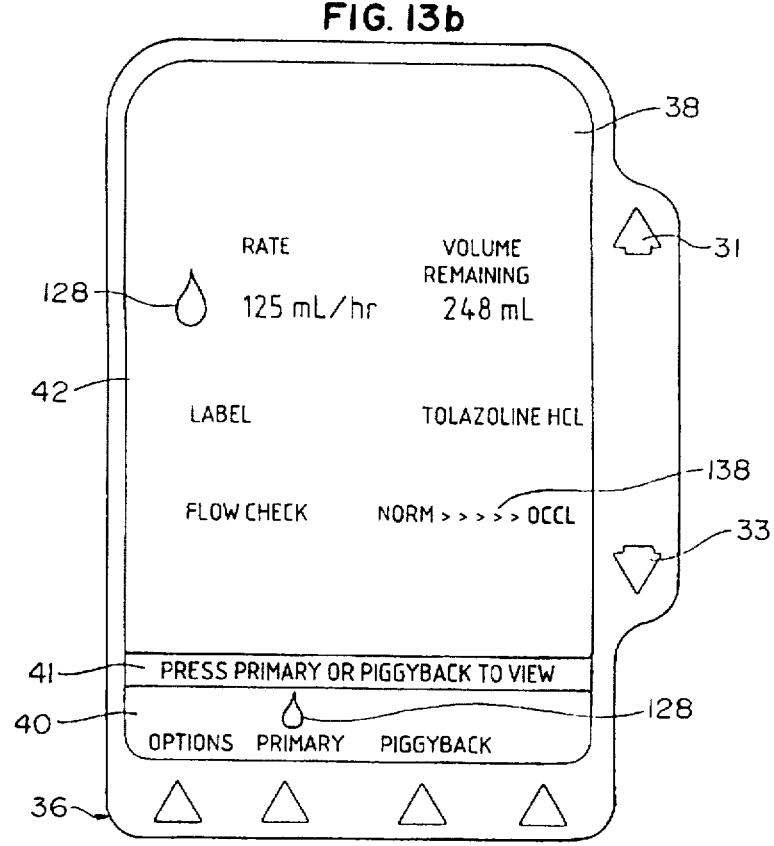

Referring to FIG. 13(b), a display area is seen which includes the flow check display feature. The flow check display feature provides the user with a graphical display of the downstream resistance to flow. In the preferred embodiment, as seen in FIG. 13(b), a plurality of triangles 138 are provided which represent the downstream flow resistance. When one triangle 138 is filled, normal flow conditions are present. When all of the triangles 138 are filled, the downstream flow has been occluded. When the downstream flow has been occluded, the occlusion alarm is enabled.

Figure 13C:
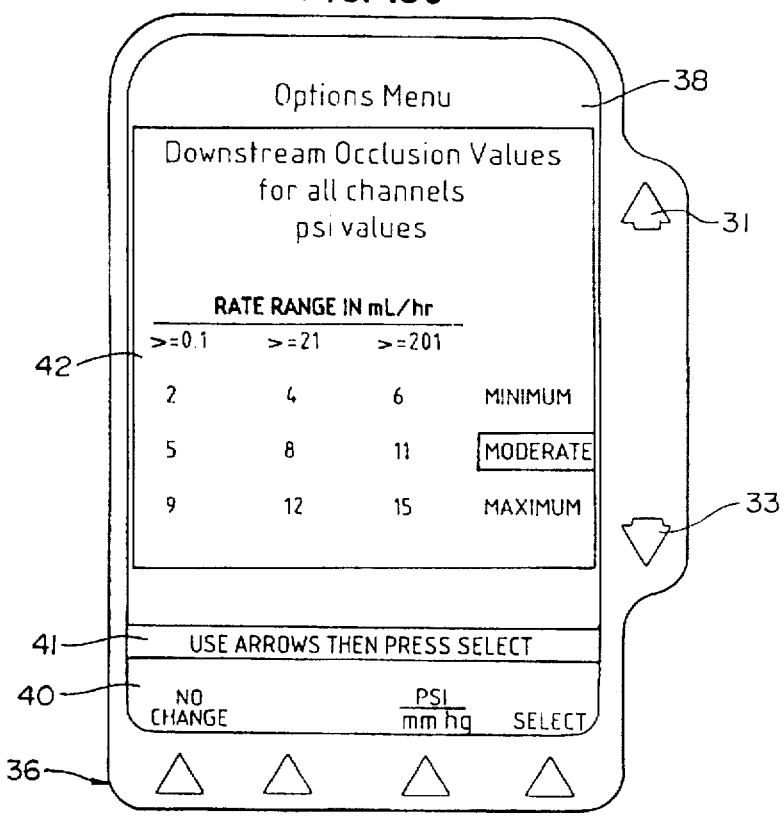

The downstream occlusion value allows a user to review and change selection of the downstream occlusion levels. On selecting the downstream occlusion value, the options menu will display a downstream occlusion value table, as seen in FIG. 13(c). The prompt line instructs the user how to change the selected values. The soft keys include a "no change" soft key, a "PSI/MMHG" soft key, and a "select" soft key. The "PSI/MMHG" soft key allows users to view the values in millimeters of mercury instead of the standard pounds per square inch. If the user wishes to change the occlusion values, the "select" soft key is pressed on the options menu, the scroll-up and scroll-down arrow keys can be used to highlight the new value range, and the "select" soft key is pressed to lock in the new selection.

Figure 13D:
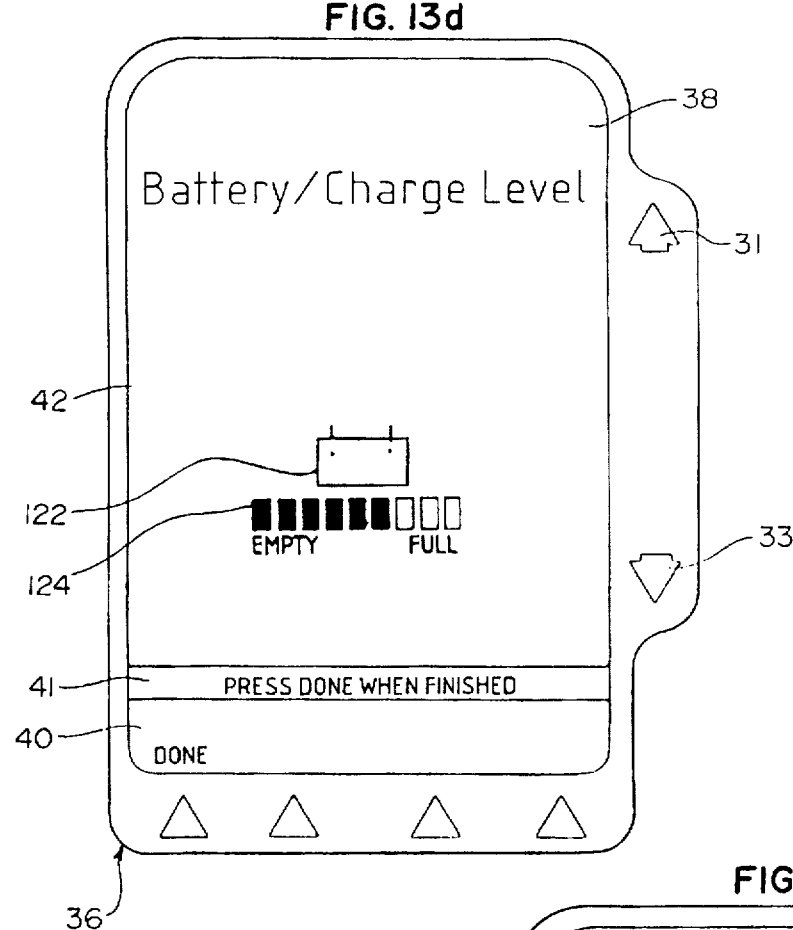

As seen in FIG. 13(d), the battery charge level on the options menu allows the user to access information regarding the battery charge level of the auxiliary battery. The battery charge icon 122 is displayed in the main display area. The prompt line instructs the user how to exit the battery charge level option. A "done" soft key is provided to exit the battery charge level display.

A final selection on the options menu is the configuration/service function. This function is made available for hospital service and upkeep personnel for pump configuration selections and for product service. Access to this function requires a pass code entry number, which is intended to be kept by authorized personnel only. This function is described in detail below.

Several additional features on the pump are described below. In FIG. 5, a "label line" soft key feature was seen. The label library allows the user to select from a list of informational labels, including solution, therapy and medications identifications. Selection of an informational label displays the selected label on the programming mode screens as well as the main display screen. The selected label also may be displayed on the channel display during infusion. This allows the user to readily identify the solution or medication being infused.

Figure 14:
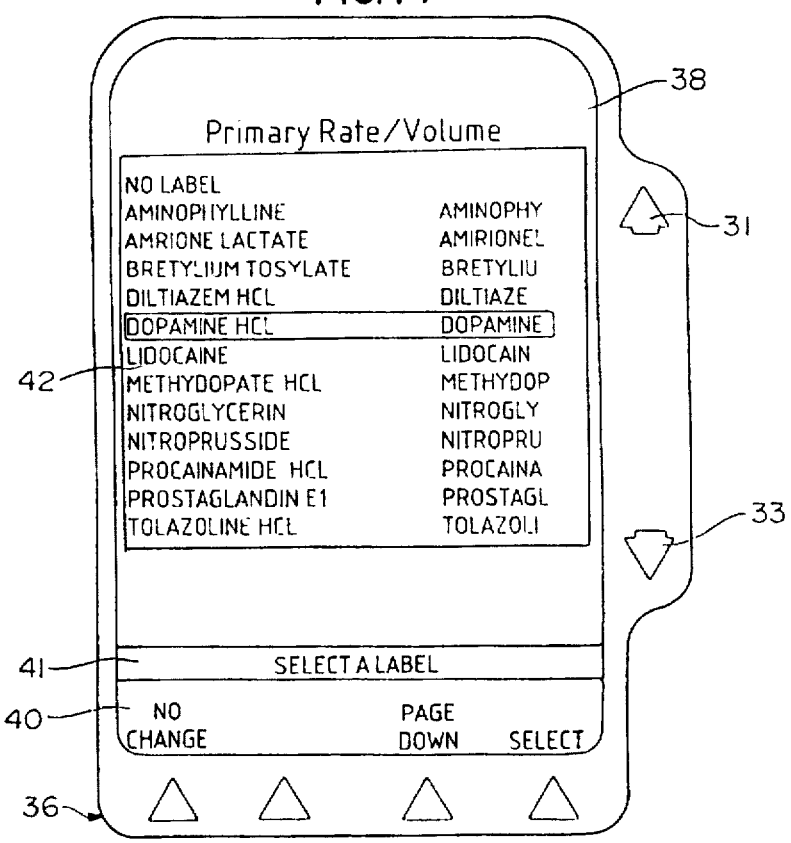

To select a label, the user selects the "label line" soft key during the programming mode. When the "label line" soft key is pressed, a pop-up screen of available labels, including the full name of the medication, therapy or solutions and the label abbreviation, will appear in the display area, an example of which is seen in FIG. 14. The prompt line instructs the user to select a label while "no change," "page up," "page down," and "select" soft keys are provided. The "page up" and "page down" soft keys are provided to enable the user to scroll if multiple screens of available labels are used. An arrow icon is provided in the lower corner if additional screens of available text are provided. An arrow icon is provided in the upper corner (not shown) if previous screens of available text are provided. The scroll-up and scroll-down arrow keys are used to highlight the desired label. The "select" soft key can then be used to select the label, with the display area automatically reverting back to the programming screen with the label selected displayed.

Figure 15:
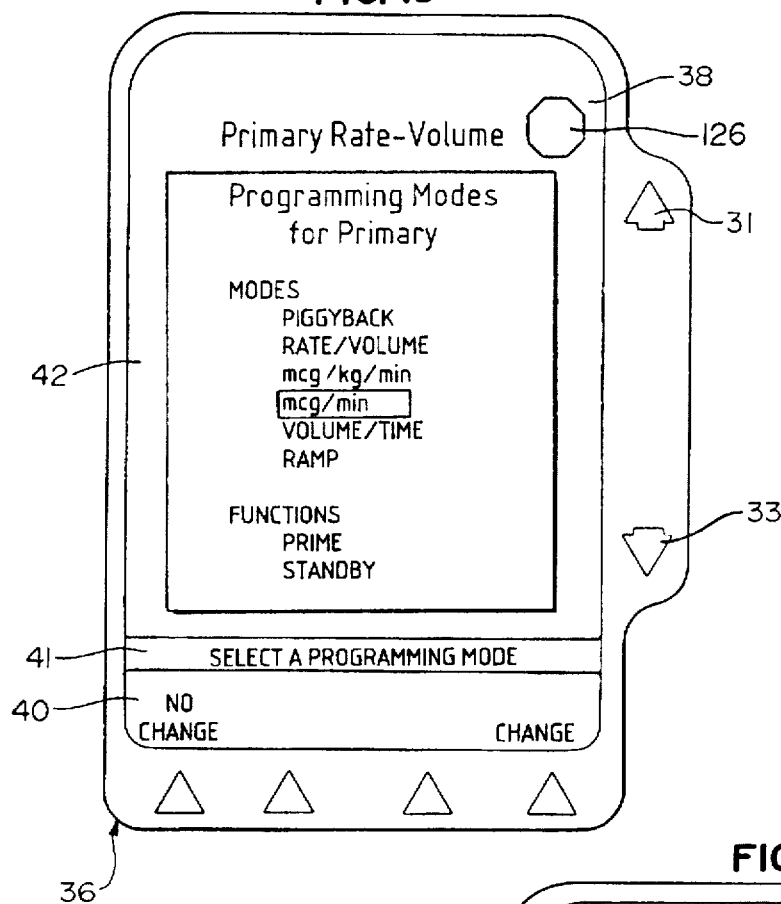

The present invention also provides several available programming modes for primary infusion. Upon selection of the "change mode" soft key in the programming mode display, if the programming mode is in the primary programming function, an change mode pop-up menu, as seen in FIG. 15, is displayed. The change mode pop-up menu includes mode and function subroutines. The mode subroutine includes the piggyback subroutine previously described, as well as user-selected programming subroutines such as rate/volume, mcg/kg/min, mcg/min, volume/time, and ramp, as described in more detail below.

Figure 16A:
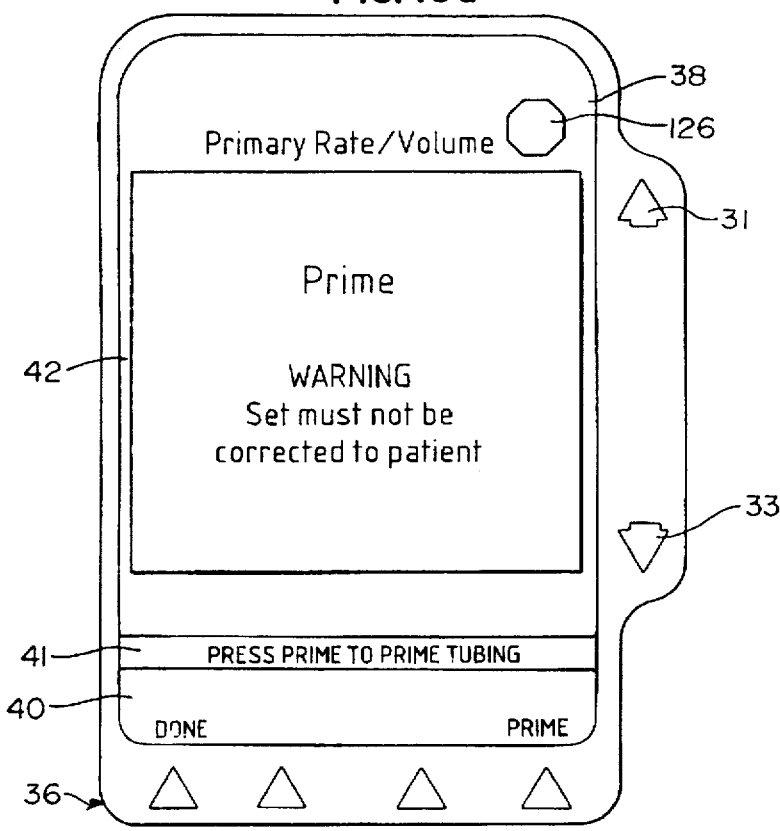

The function subroutine includes prime subroutine and standby subroutine. The prime subroutine is used to assist users in priming the IV tube in order to ensure that no air is in the IV tube prior to infusion. In the primary programming mode, after the IV tube has been loaded, the prime subroutine is accessed by pressing the "change mode" soft key. The scroll-up and scrolldown arrow keys can be employed to highlight the prime field, which can be selected by pressing the "select" soft key. The display area then displays the prime pop-up message, as seen in FIG. 16(a). The prompt line instructs the user to press the "prime" soft key to prime the IV tube. A "done" soft key also is provided to indicate when the prime function has been completed. While priming is active, the display area shows the prime pop-up message seen in FIG. 16(b). Pressing the "done" soft key upon completion of priming returns the display area to the primary infusion program.

Figure 17B:
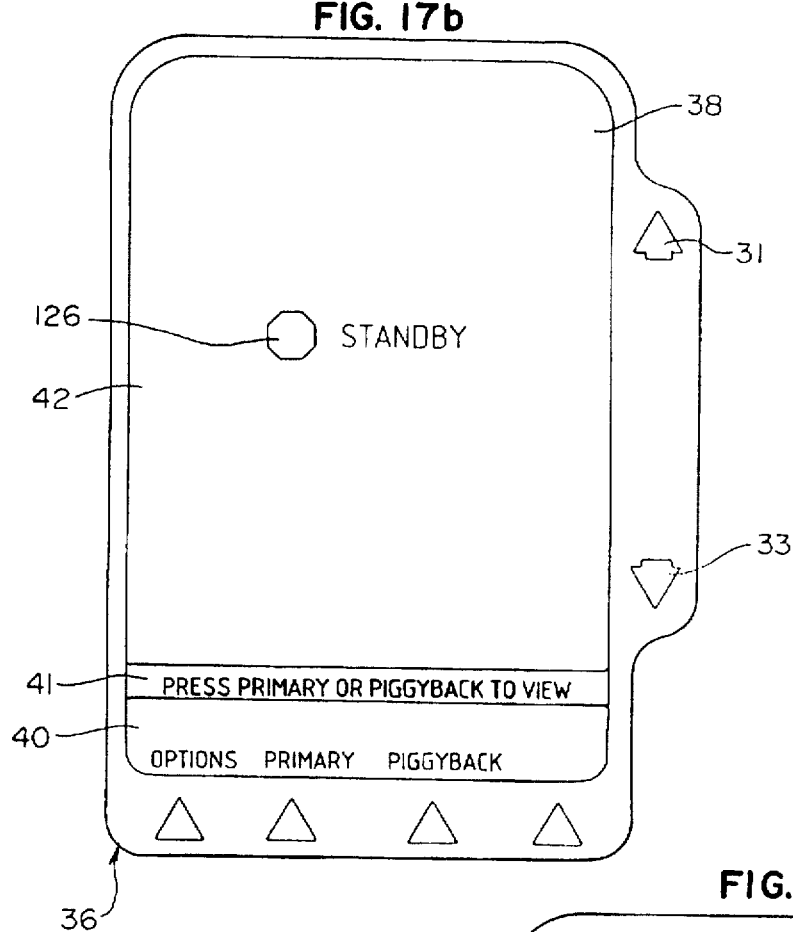

The standby subroutine allows programming of the pump without starting the infusion. Thus, the standby subroutine disables the channel stop alert notification. To access the standby subroutine, the scroll-up and scroll-down arrow keys are used to highlight the standby function in the change mode pop-up window. The "select" soft key is selected, which causes the standby pop-up message seen in FIG. 17(a) to appear on the display area. After a brief, predetermined time, the main display screen reappears. However, as seen in FIG. 17(b), standby is displayed where the program information normally appears. Pressing the "primary" soft key, the "piggyback" soft key, the rate key or the volume key disables the standby function. When disabled, the display returns to the programming routine, based upon which disabling key was selected.

As previously noted, several of the operating routines relate to the optional dose programming subroutines. These subroutines allow the user to program the dose of a primary infusion independent of patient parameters, based on patient body weight or based upon patient body surface area. For example, the dose programs which are independent of the patient parameters include mg/hr, mg/min, mcg/min, mcg/hr, units/hr, and units/min. Examples of dose programs which are based on patient body weight include mg/kg/hr, mg/kg/min, mcg/kg/hr, mcg/kg/min, units/kg/hr, and units/kg/min. Examples of dose programs which are based on patient body surface area include mg/m$^2$/hr, mcg/m$^2$/hr, and units/m$^2$/hr.

In the optional dose programming subroutines, when two of three parameters have been entered, the master microprocessor will calculate the final parameter. For example, if the dose has been entered and the concentration of the drug has been entered or calculated, as described below, the master microprocessor will calculate and display the rate. Similarly, if the rate has been entered and the concentration of the drug has been entered or calculated, the master microprocessor will calculate and display the dose. After the necessary parameters have been entered and the dose or rate calculated, if the dose or rate values are changed, the master microprocessor will automatically recalculate and display the new values.

Figure 18A:
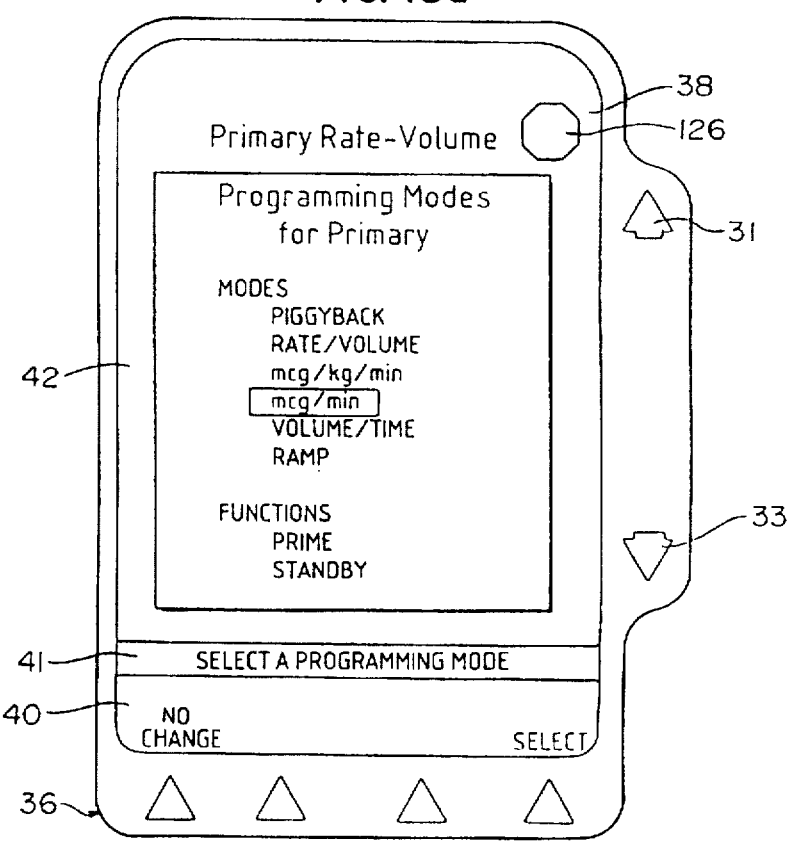
Figure 18B:
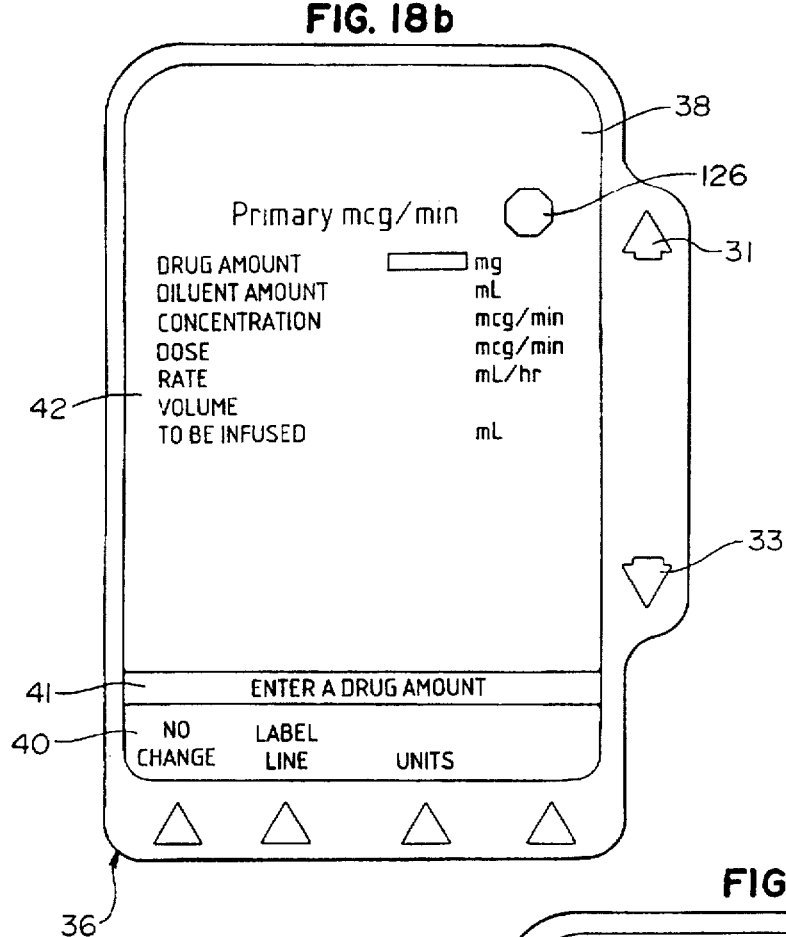

If the concentration of the drug to be administered is known by the user, it can be directly input into the infusion pump. If the concentration is not known, the user can enter the drug amount and diluent volume, and the master microprocessor will automatically calculate and display the concentration. Referring now to FIG. 18, the programming of the infusion pump is described. From the primary programming modes, the user uses the scroll-up and scroll-down arrow keys on the change mode menu to highlight the appropriate dose formula selection from the examples previously set forth above, an example of which is seen in FIG. 18(a). The prompt line instructs the user to select the programming mode. To select a programming mode, the desired mode is highlighted and the "select" soft key is pressed. The display area then displays the dose programming screen seen in FIG. 18(b).

Figure 18C:
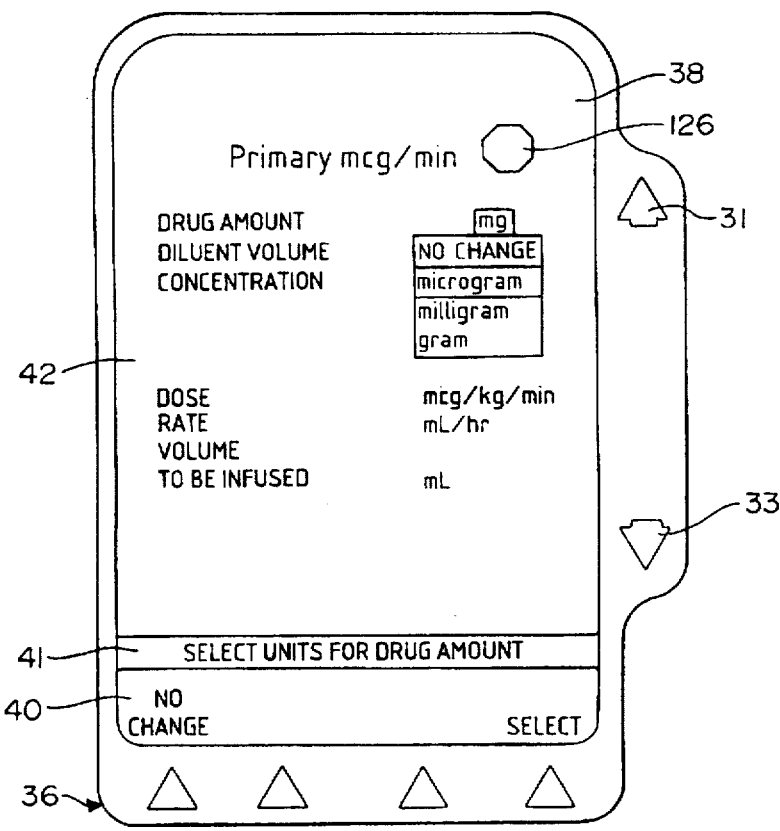
Figure 18D:
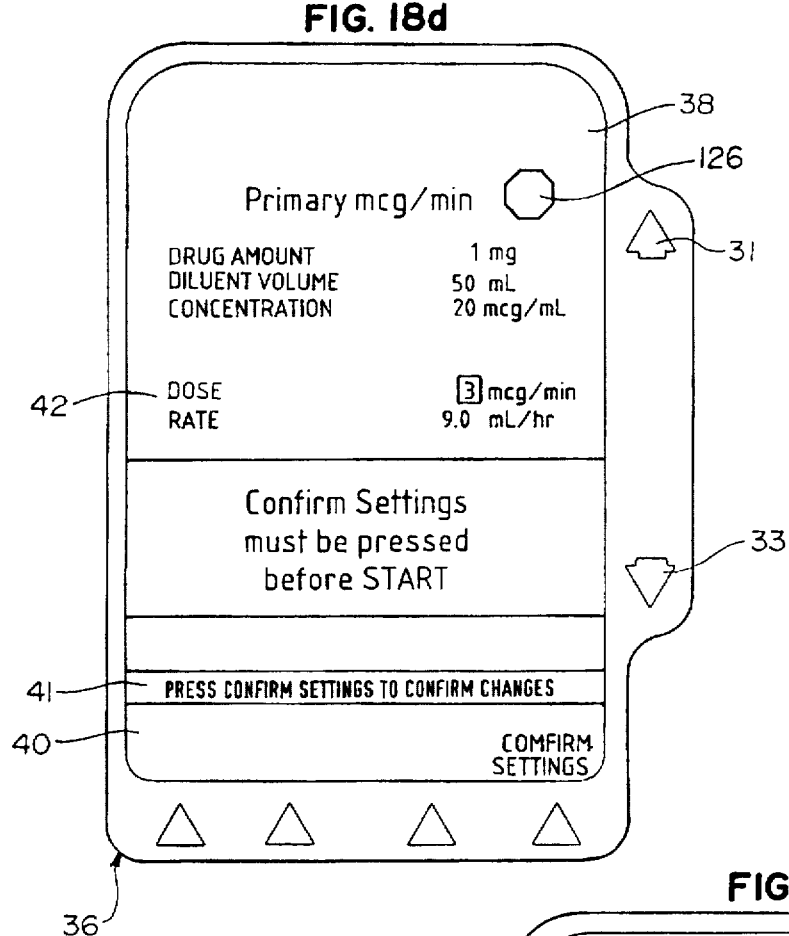

If a dose infusion has been retained in the program memory, the screen will initially display the parameters from that infusion. To clear the displayed parameters, a "clear settings" soft key is pressed. The dose programming screen includes a prompt line which instructs the user to enter the amount in the highlighted field. "Change mode," "label line," and "units" soft keys are provided. The dose programming screen includes the measuring units for each of the categories of dose information. If the user wants to enter different units than those displayed for fields with more than one measuring unit, the "units" soft key is pressed to bring up the unit change list screen, an example of which is seen in FIG. 18(c). The scroll-up and scroll-down arrow keys are used to highlight the desired units, with the select key pressed to change to the desired units. Upon selection of the alternative units, the dose programming screen is again displayed. On the dose programming screen, the initial parameter is highlighted for entry by the user.

Again, the scroll-up and scroll-down arrow keys can be utilized to move the highlighted portion into the desired category. For example, if the concentration is known, the scroll-up and scroll-down arrow keys can be used to highlight the concentration parameter and the concentration can be entered. This eliminates the need to enter the drug amount and diluent volume parameters. If the concentration is not known, the scroll-up and scroll-down arrow keys can be used to highlight and enter the drug amount and diluent volume parameter, with the master microprocessor then calculating and displaying the concentration. The scroll-up and scroll-down arrow keys can then be used to highlight and enter the dose field or to highlight and enter the rate value, with the master microprocessor calculating the unknown parameter.

Prior to starting the infusion, the user must confirm the calculated settings. If the user does not, the display area goes to the confirmed settings message window seen in FIG. 18(d). The prompt line instructs the user to confirm the setting by pressing the "confirm setting" soft key. After the settings have been confirmed, the infusion is started by pressing the start key, as previous described. The display area returns to the main display which, as set forth above, displays the rate, the volume remaining to be infused, and/or the time remaining for the infusion, as well as the dose.

Figure 19:
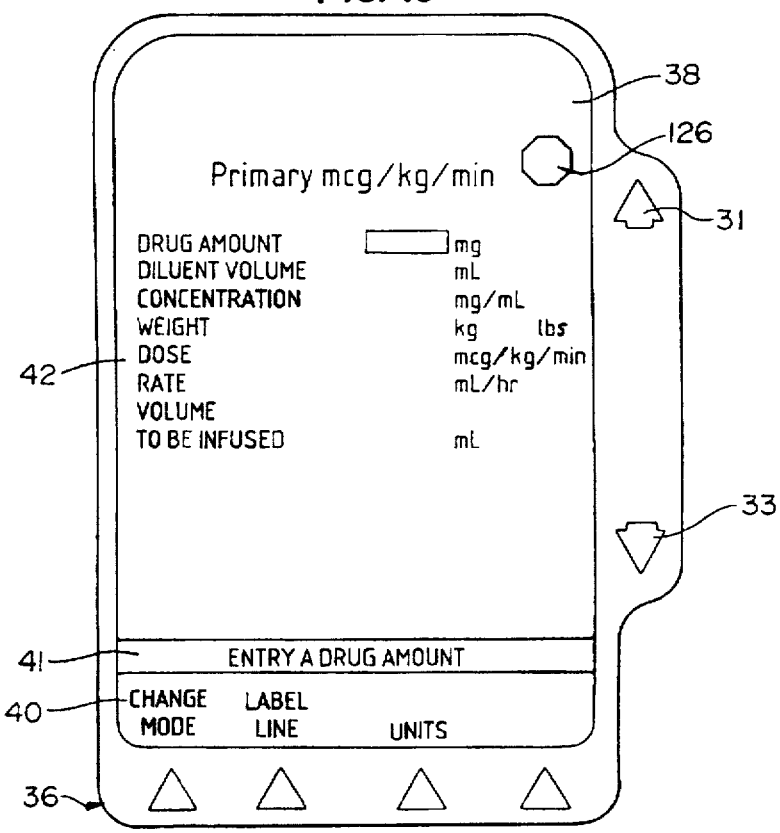

If the optional dose programming function is utilized based on patient weight, a similar programming subroutine is utilized. Referring to FIG. 19, a dose programming screen having parameters related to programming based on the patient's weight is seen. In addition to the programming values previously described, the patient's weight must be programmed by entering a value using the numeric key pad. The value can be entered utilizing either kilograms or pounds, with the units selected by using the "units" soft key to highlight the appropriate selected unit.

Figure 20:
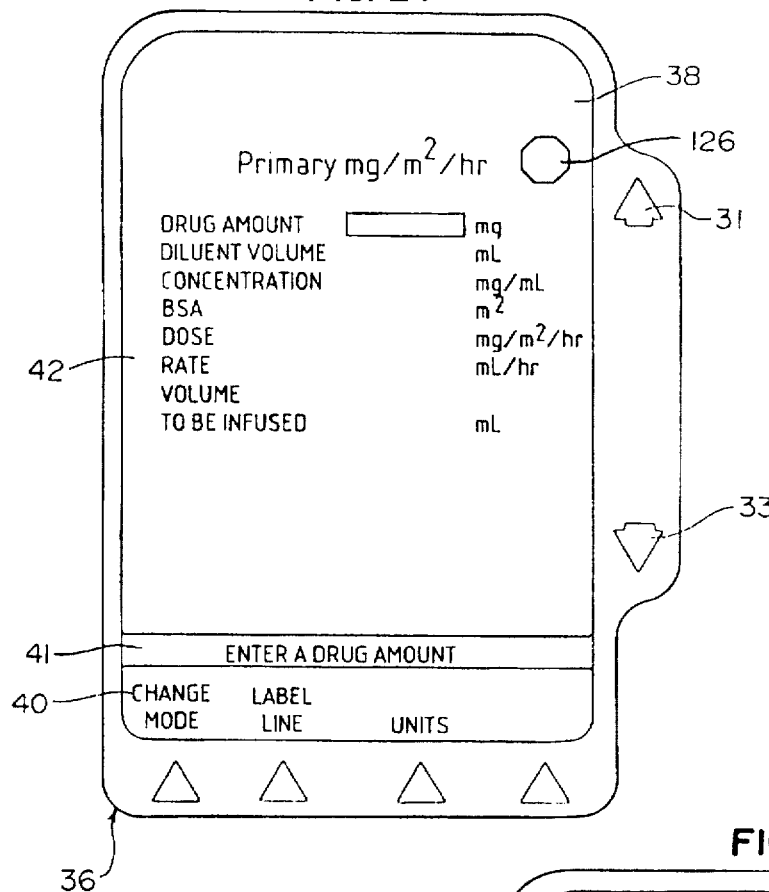

Similarly, if an optional dose programming function is selected based on patient body surface area, a dose programming screen is used which includes parameters directed to this function. In addition to the programming of each function as previously described, the dose programming screen includes the patient's body surface area (BSA) parameter, as seen in FIG. 20. This BSA parameter is used by the master microprocessor to calculate the dose or rate utilizing a BSA calculation known in the art.

Figure 21A:
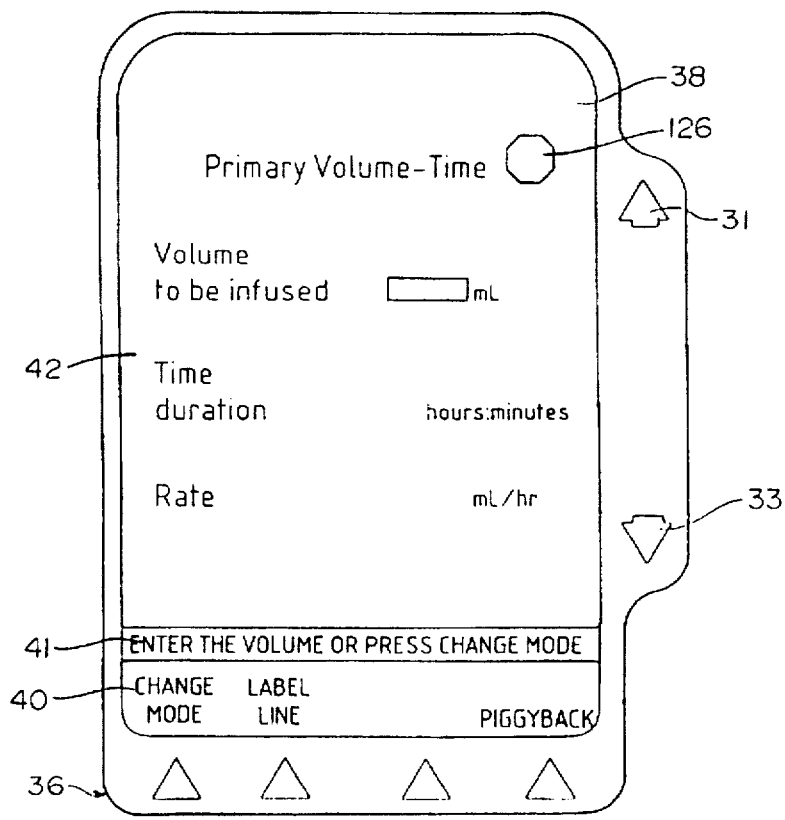
Figure 21B:
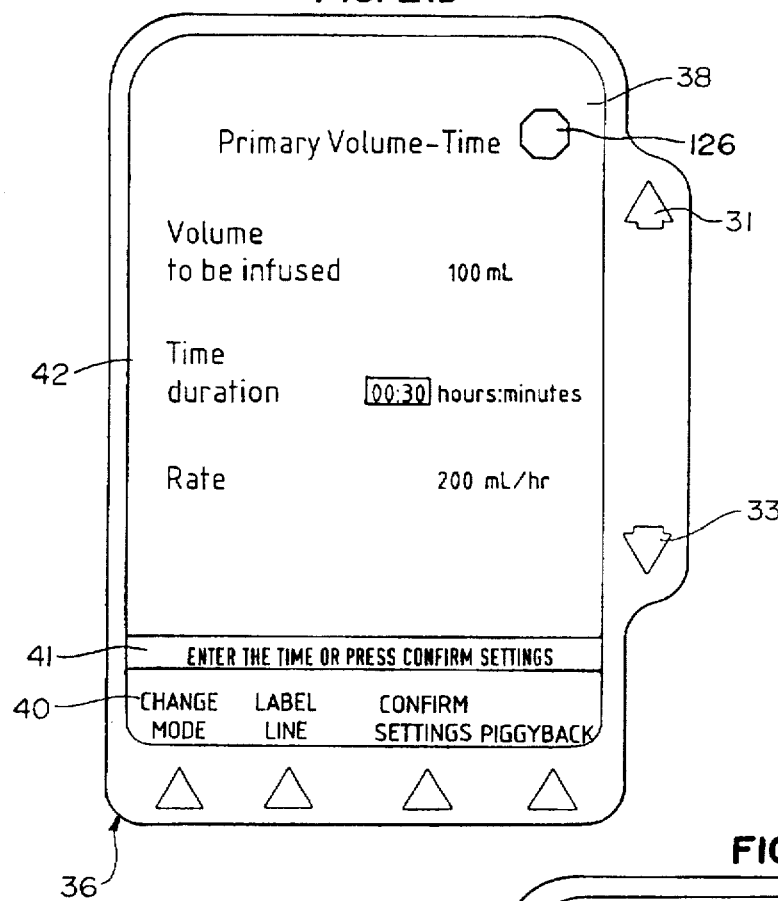

Optionally, the pump can be programmed utilizing the volume to be infused and time of infusion parameter, with the master microprocessor calculating the flow rate. This feature is available in both the primary and piggyback modes. To access the volume/time programming function, the "change mode" soft key is selected, as seen in FIG. 21(a). A volume/time programming screen is used, having parameters related to programming based on the volume to be infused and the time of infusion. Utilizing the scroll-up and scroll-down arrow keys, values can be entered for the volume to be infused and the time for infusion. The pump then automatically calculates and displays the flow rate. As seen in FIG. 21 (b), to begin infusing, the "confirm settings" soft key is pressed to confirm the entered values as well as the calculated flow rate, and the start key is pressed.

The ramp mode allows the user to enter a total volume for infusion and up to four individual time parameters. These time parameters include run time, delay time, ramp-up time, and ramp-down time. Run time includes both the ramp-up and ramp-down time parameters as well as the additional level delivery time. Delay time is the time prior to ramp-up, when the device runs at a preselected KVO rate. Ramp-up time is the time established for the device to ramp up to the level delivery rate. Ramp-down is the time established for the device to ramp down from the level delivery rate to the KVO rate.

Figure 22A:
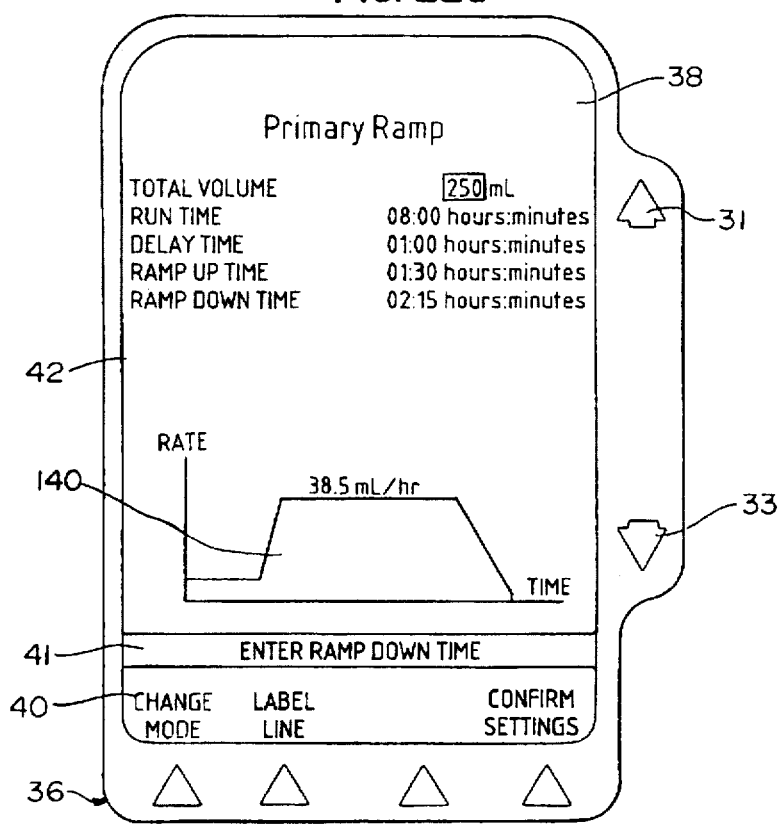

From the entered parameters, the master microprocessor calculates the rates necessary to perform the time and volume requirements. The total volume includes the volume infused during the ramp-up, level delivery, and ramp-down times as well as the volume delivered during the KVO delay time. As such, volume delivered during the ramp-up, level delivery, and rampdown times is calculated based on the total volume to be infused less the volume delivered during delay time. As seen in FIG. 22(a), the ramp programming screen includes the total volume, run time, delay time, ramp-up time, and ramp-down time. These parameters can be entered utilizing the scroll-up and scroll-down arrow keys to highlight the appropriate field. When all of the required values have been entered, the pump will calculate the level delivery rate. The level delivery rate will be displayed above a ramp delivery icon 140. The "confirm settings" soft key confirms the entered values as well as the calculated level delivery rate. To begin infusing, the start key is pressed.

Figure 22B:
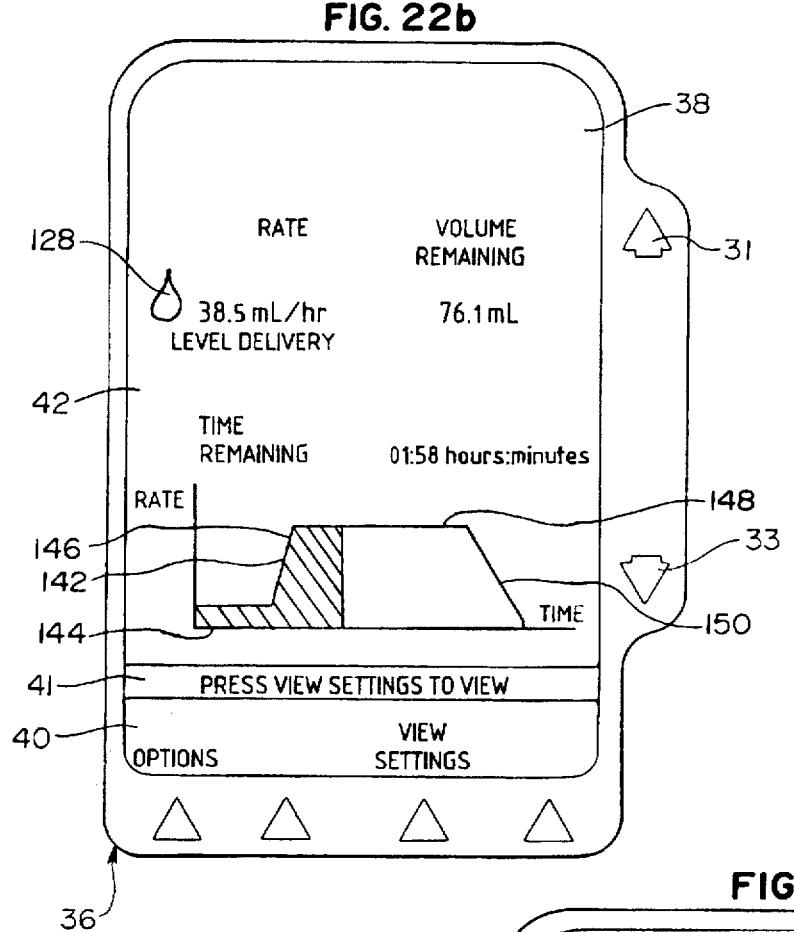
Figure 22C:
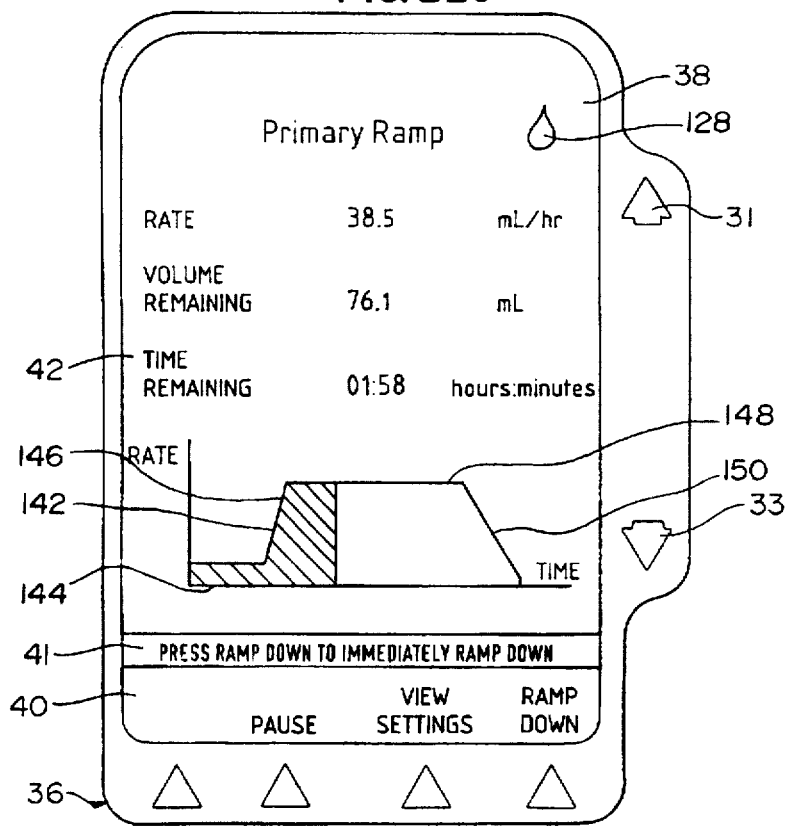

While the pump is infusing in the ramp mode, the current rate of infusion, the delivery phase, the volume remaining to be infused, and the time remaining for the infusion are displayed, as seen in FIG. 22(b). The main display also includes the ramp status icon 142. The ramp status icon 142 includes a likeness of the stages of the ramp infusion, including the delay time 144, the ramp-up 146, the level delivery 148, and the ramp-down 150 periods. During infusion, the ramp status icon 142 is continually updated to show the progression of the therapy. The portion of the ramp infusion that is completed is shown shaded in black. The prompt line includes the user instructions to view the settings for the ramp infusion. Upon pushing the "view setting" soft key from the programming screen, a ramp infusion parameter screen shows the entered parameters for the ramp infusion. If the "view settings" soft key is chosen during a ramp infusion from the main display, a ramp-in-progress screen, which includes the rate, volume, and time as well as the ramp status icon 142, is displayed, as seen in FIG. 22(c). The prompt line in the display area includes options available to the user depending upon the status of the ramp infusion. In the example of the status depicted in FIG. 22(c), during level delivery the option available to the user is to immediately ramp down. Thus, a "ramp down" soft key is provided.

In order to utilize the optional drop sensor, the drop sensor is connected to the drop sensor connector. The drop sensor is attached to the drip chamber above the fluid level on the IV tube connected to the primary source fluid container. When the drop sensor senses that the primary-source fluid container is empty, a container-empty alert will occur and the device will infuse at the KVO rate during the alert. A container empty alarm will follow the container empty alert. If the optional drop sensor is utilized, the primary-volume-to-be-infused field is not mandatory. If the primary-volume-to-be-infused field is not entered, the infusion pump will operate at the program rate until the drop sensor detects an empty fluid container.

Figure 23:
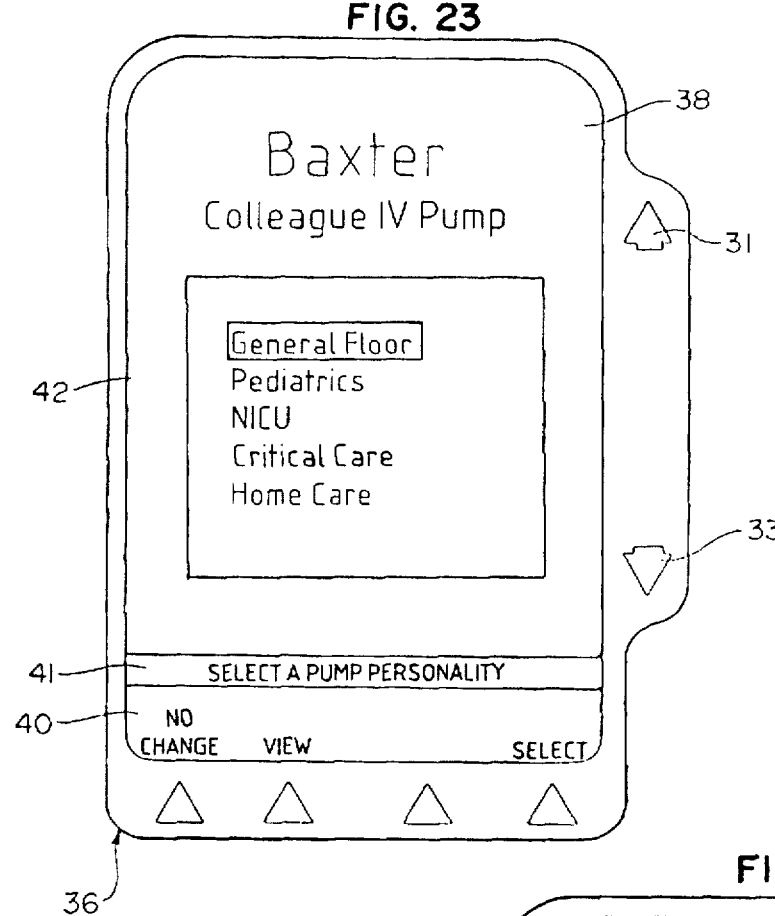
Figure 24:
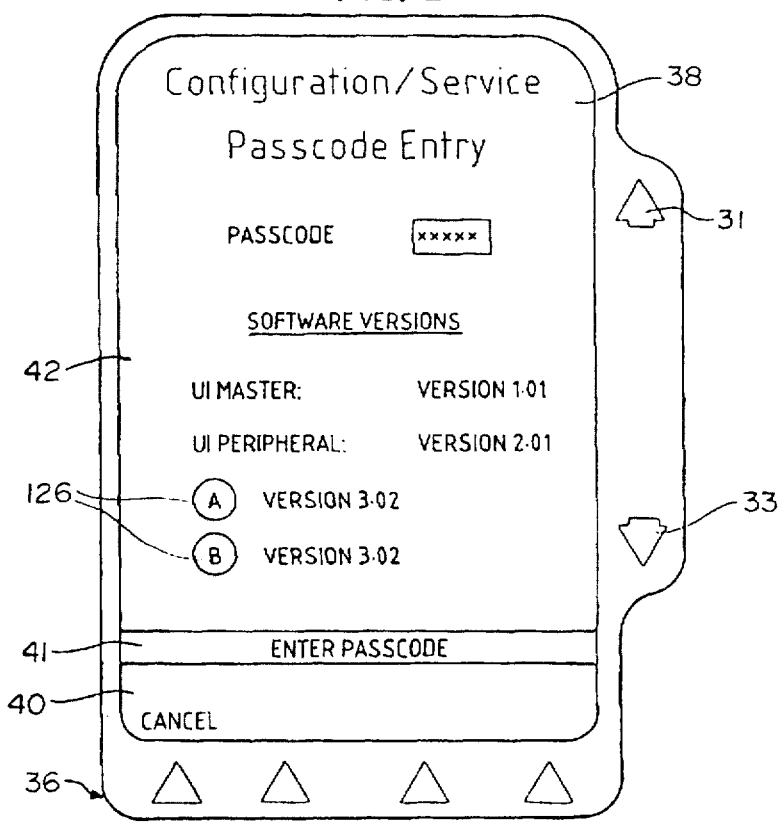

The pump is capable of functioning in a variety of clinical uses from basic through advanced programming functions. In order to facilitate usage in the selected clinical application, the present invention includes a variety of configurable sets of configuration parameters. In order to access the custom set of configuration parameters screen, the "change personalities" soft key from the power-on screen is pressed. In FIG. 23, examples of custom sets of configuration parameters such as the general floor, pediatrics, neonatal intensive care (NICU), critical care (ICU), and home care are listed. To choose a particular set of configuration parameters, the scroll-up and scroll-down arrow keys highlight the chosen set of configuration parameters. To view the configuration of any of the chosen sets of configuration parameters, the "view" soft key is pressed to display a Personality™ configuration screen. To chose a set of configuration parameters, the "select" soft key is pressed.

To configure the sets of configuration parameters, the configuration/service function of the options menu seen in FIG. 13(a) is selected. Upon selection of the configuration/service function, a password entry screen seen in FIG. 24 appears. The password ensures that only proper hospital personnel access the configuration/service routine. The prompt line directs entry of the password. The authorized personnel enter a numeral password in order to proceed in the configuration/service routine. The password entry screen includes a reference listing of the software version in the infusion pump. A "cancel" soft key is provided to exit the routine.

Figure 25A:
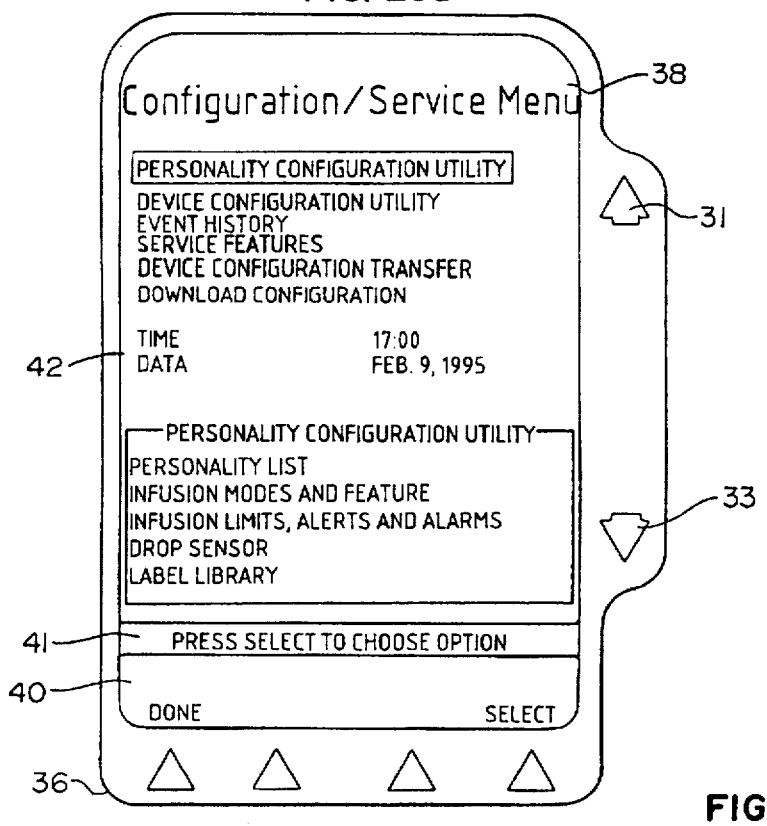

Upon successful entry of a valid password, a configuration/service menu screen as seen in FIG. 25(a) appears. The options include Personality™ configuration utility, device configuration utility, event history, service features, device configuration transfer, download configuration, time set and date set. The device configuration transfer allows the authorized hospital personnel to transfer the configuration of one infusion pump to another infusion pump. The download configuration allows the authorized hospital personnel to download the infusion pump configuration through the serial port. The configuration service menu includes a "select" soft key and a "done" soft key. When an option is highlighted, a message appears giving the particular components of an option. In the example seen in FIG. 25(a), the Personality™ configuration utility includes as components a Personality™ list, infusion modes and features, infusion limit alerts and alarms, drop sensors, and label library.

Figure 25B:
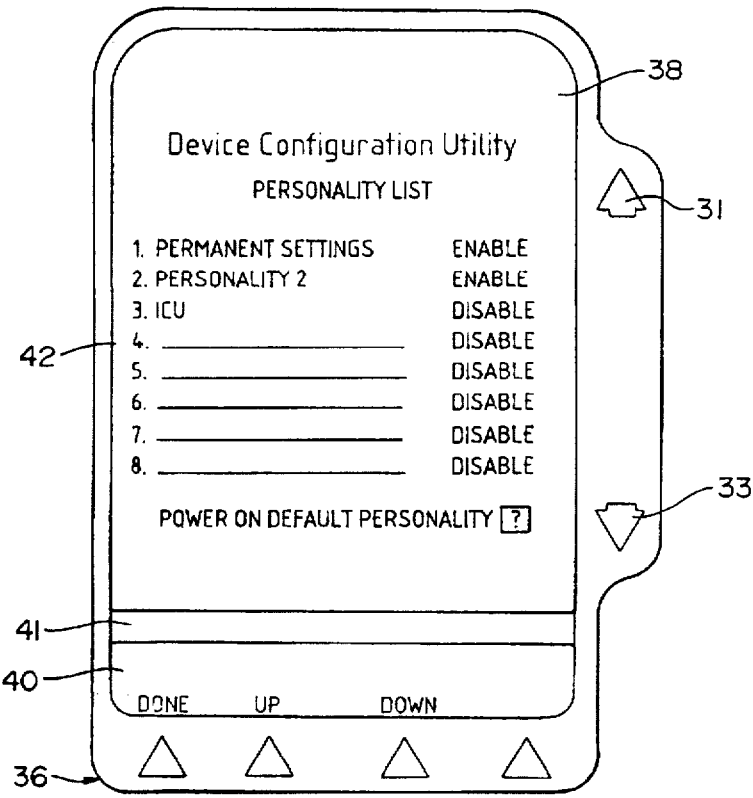

When the Personality™ configuration utility screen is entered, a Personality™ list is displayed as seen in FIG. 25(b). The power-on default set of configuration parameters is identified in the display. "Done," "up" and "down" soft keys appear. Upon highlighting a set of configuration parameters, a "change settings" soft key, an "enable/disable" soft key, and a "copy Personality™" soft key appear. The authorized hospital personnel can modify or view the set of configuration parameters by using the "change settings" soft key, modify the name of the set of configuration parameters by using the "change settings" soft key, copy the configuration of the set of configuration parameters by selecting the "copy Personality™" soft key, or enable or disable the set of configuration parameters by using the "enable/disable" soft key. When a set of configuration parameters is enabled, it will appear listed in the list of sets of configuration parameters when the "new Personality™" soft key is pressed after power-on.

Figure 25C:
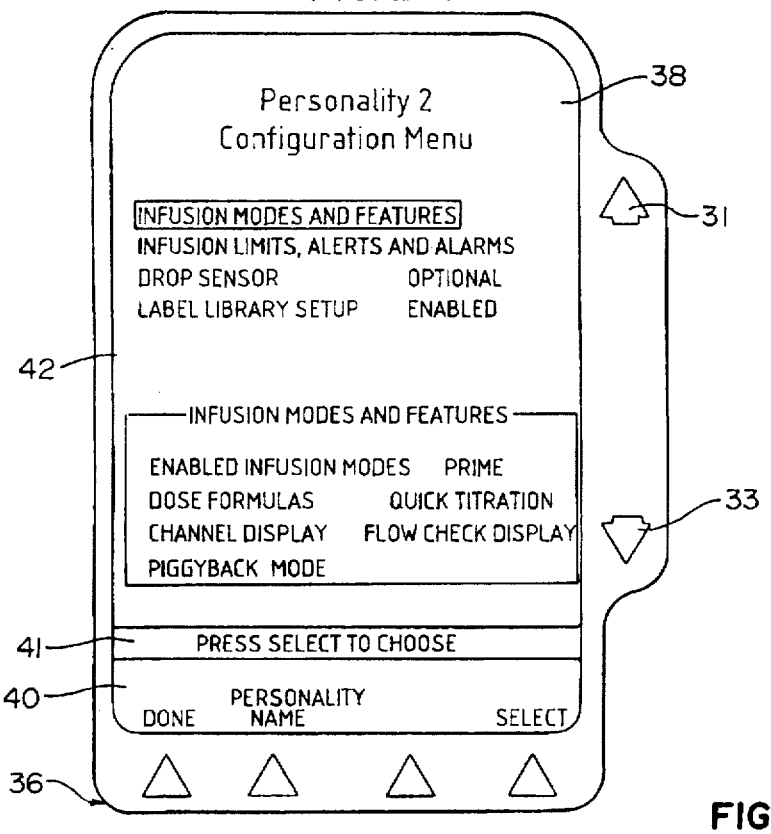
Figure 25D:
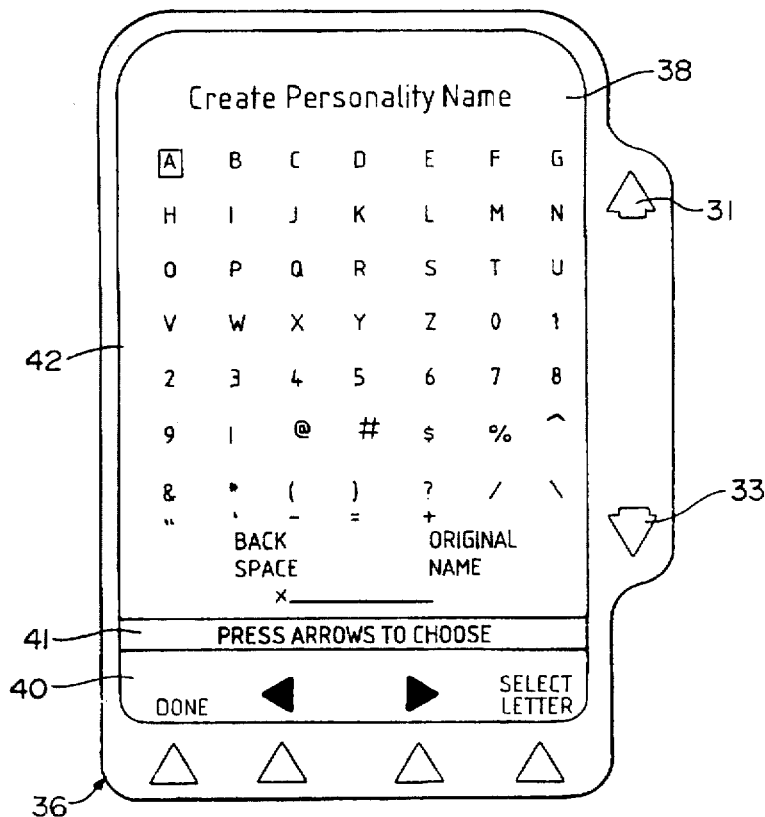

If the "change settings" soft key is selected, a Personality™ configuration menu for the selected set of configuration parameters is displayed, an example of which is seen in FIG. 25(c). The Personality™ configuration menu identifies the components. A message identifies the configurable items found in the highlighted component. The soft keys include a "done" soft key, a "select" soft key, and a "Personality™ name" soft key. Selection of the "Personality™ name" soft key displays the create name screen seen in FIG. 25(d). Using the soft keys and the scrollup and scroll-down arrow keys, authorized hospital personnel can enter the name of a set of configuration parameters.

Selection of the infusion mode and features, for example, allows the authorized hospital personnel to determine which features and functions will be available for the clinical user for that set of configuration parameters and how the infusion pump will display features and functions to the clinical user. Examples include disable infusion modes, disable dose formulae, set channel display, disable piggyback mode, disable prime mode, enable quick titration, and enable flow check display.

Figure 26A:
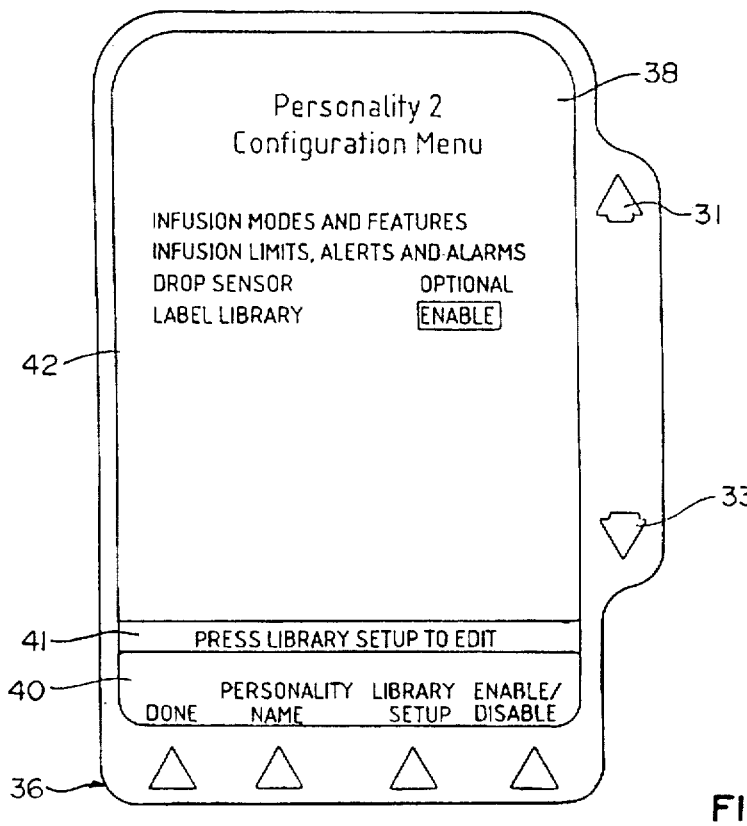
Figure 26B:
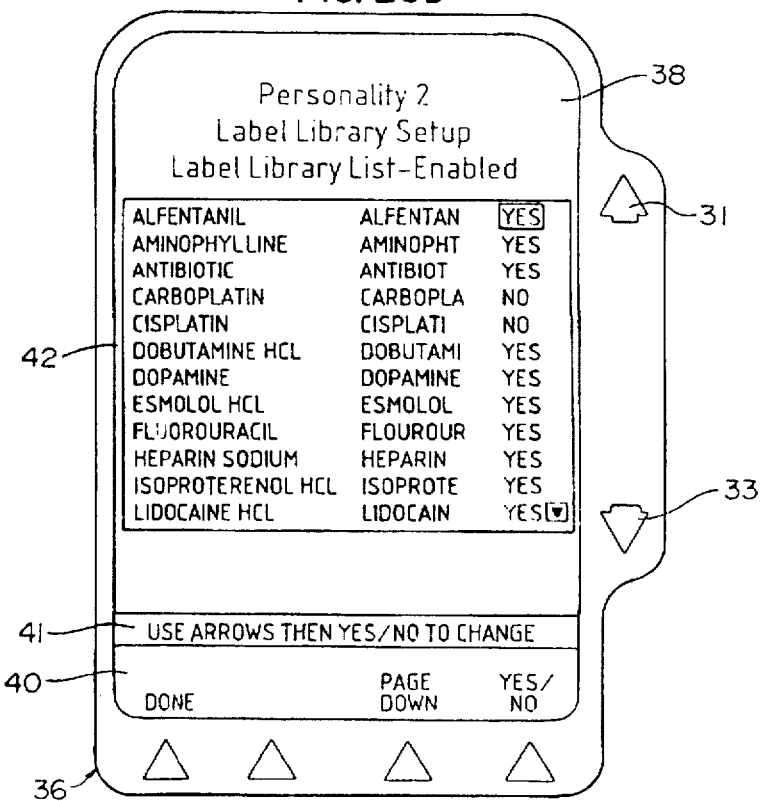

The authorized hospital personnel can enable or disable the label library. The authorized hospital personnel also can select which medication or solution names are available to the clinical user for selection if the label library is enabled. When the label library is highlighted in the configuration menu seen in FIG. 26(a), "done," "library set up" and "enable/disable" soft keys are provided. Upon selection of the "library set up" soft key, the label library set-up list is displayed, as seen in FIG. 26(b). A "yes/no" soft key is provided to enable or disable labels.

The present invention also provides several troubleshooting alert, alarm and failure messages. When an alert, alarm or failure message occurs, the status area of the display, as well as the pump module character display, identify the alert, alarm or failure. Alert messages may require a user intervention, but do not stop the infusion. Alarm conditions automatically stop the infusion and require immediate attention before infusion can be restarted. A device failure automatically stops any infusion. An alarm condition overrides an existing alert condition while a failure overrides all alerts and alarms. An alert condition lights the yellow alert LED beneath the pump module display, and sounds the alert tone. The alert tone can be silenced for a period of time, such as for example two minutes, by pressing the silence key.

The alert conditions include advanced air alert which indicates that the user is advancing a detected air bubble. A battery-low alert indicates that the auxiliary battery has less than a predetermined amount of infusion time left. This alert occurs before the battery alarm condition, discussed below, occurs. The changing piggyback alert indicates that the piggyback rate is being changed or a label is being added. The changing primary alert indicates that a primary rate or dose is being changed or label is being added during an infusion.

The channel-stopped alert indicates that the pump is on, not in standby mode, but the infusion is not running. This alert is designed to remind the user to start the pump infusion or to power-off the pump. The container-empty alert indicates that the drop sensor accessory has sensed that the source container is empty and the device is infusing at the lower of the KVO rate or the preprogrammed rate. The KVO alert indicates that the programmed volume to be infused has been completed. The piggyback-callback alert indicates that the piggyback infusion has been completed and the pump has switched to the primary infusion. To continue primary infusion, the silence key can be pressed. The prime alert indicates that the priming module is being employed. The programming-piggyback alert indicates that a piggyback infusion is being programmed while a primary infusion is taking place. This alert is intended as a reminder to the user to complete the piggyback program and start the piggyback infusion, if appropriate. The ramppaused alert indicates that a ramp infusion has been paused. This reminds the user to press the start key to resume the ramp or to press the "cancel ramp" soft key to cancel the infusion.

Figure 27A:
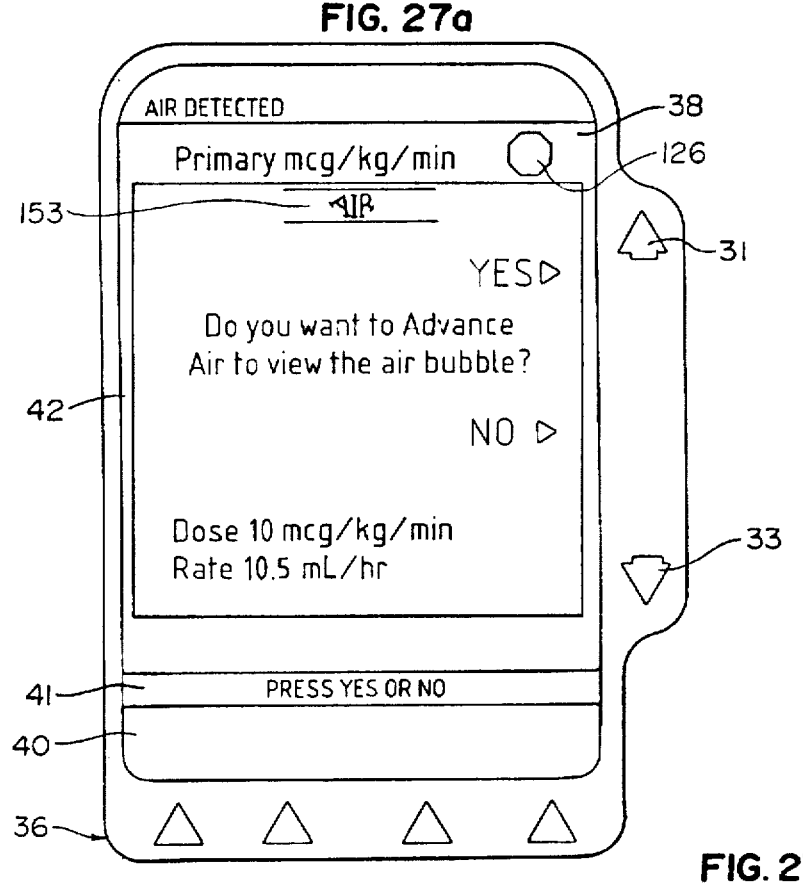
Figure 27B:
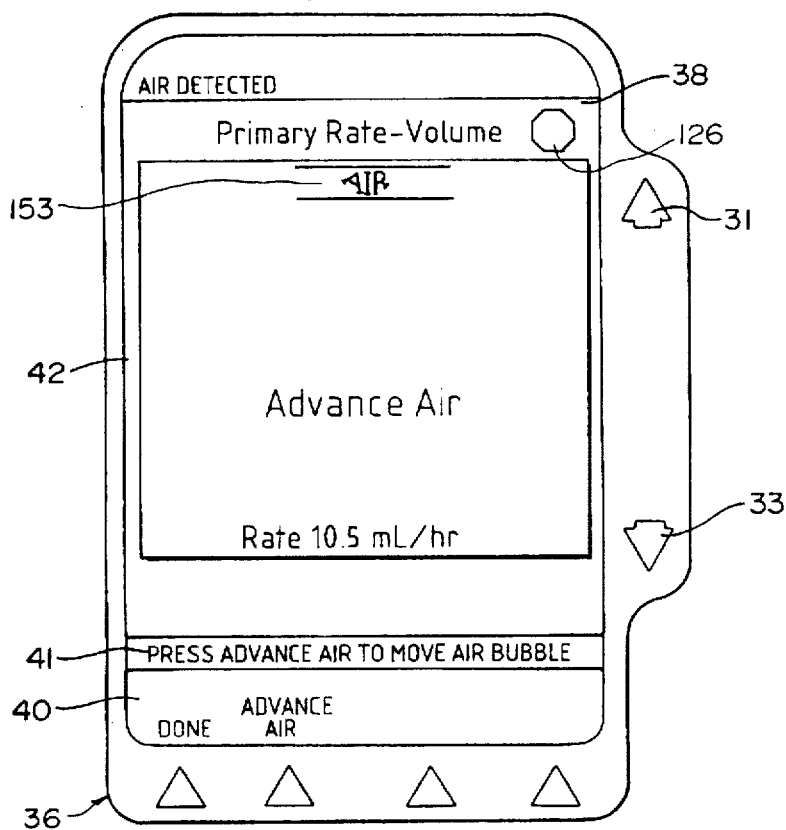
Figure 27C:
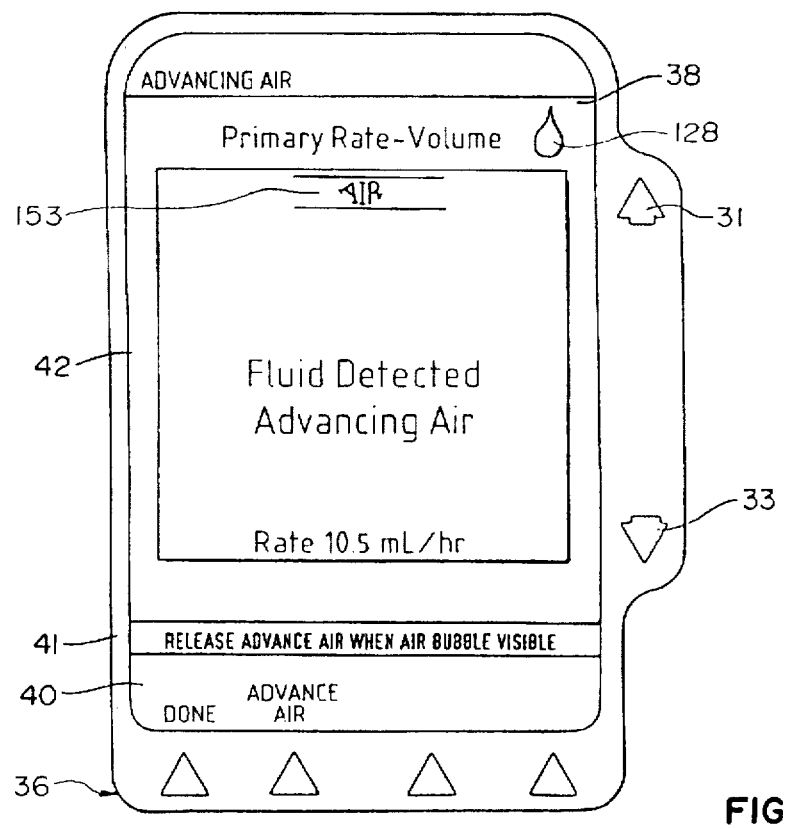
Figure 27D:
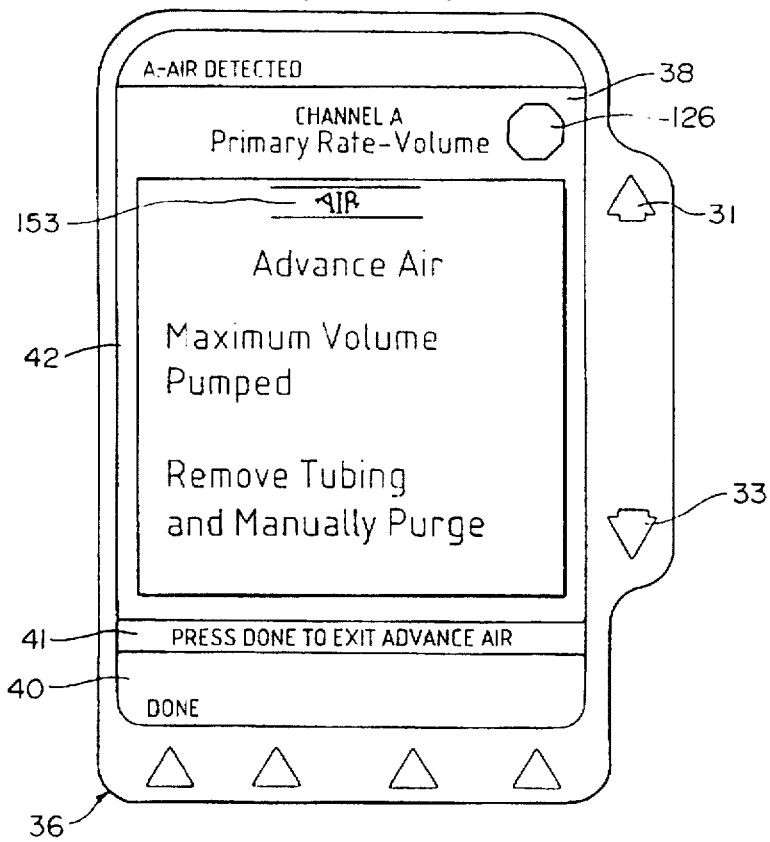

The air-detect alarm indicates that an air bubble has been detected based on preprogrammed air bubble detection parameters. The display area displays the air-in-line icon 153 and the user is asked if the advance air feature is desired to be used to view the air bubble, as seen in FIG. 27(a). Choosing the advance air feature advances the display screen to the "advance air" screen depicted in FIG. 27(b). To advance the air bubble, the user presses and holds the "advance air" soft key. When the air-detect feature again detects fluid, the display area will inform the user of the fluid detection by displaying the fluid icon 155, seen in FIG. 27(c). The user can continue to advance the air bubble until it is at the injection site on the tubing, where it can be removed using a syringe. Upon sensing fluid at the air sensor location and the appearance of the fluid icon 155, the alarm condition has been reset and the infusion can be restarted by pressing the start key. A user can advance air until a maximum defined volume has been pumped. Once this maximum volume has been pumped, the display informs the clinical user, as seen in FIG. 27(d). The IV tube should be removed and manually purged to reset the alarm.

The battery-depleted alarm indicates that the auxiliary battery charge has diminished below the level necessary to continue infusion. To reset this alarm, the pump must be plugged into an AC supply. The check-drop-sensor alarm indicates that, if the pump has been configured for mandatory drop sensor use, the sensor has not been connected. To reset this alarm, the drop sensor must be connected. The downstream-occlusion alarm indicates that a downstream occlusion, such as a closed distal flow clamp, has occurred. To reset this alarm, the downstream occlusion must be removed. If the pump is configured with the auto restart feature, the pump will automatically restart if the occlusion has been removed within a predetermined period of time after occlusion detection.

The drop sensor malfunction alarm indicates that the drop sensor either has been improperly positioned on the drip chamber in the IV tube or has been damaged. To reset this alarm, the drop sensor must be properly positioned or repaired if damaged. The flow-detectedon-primary alarm indicates that the drop sensor has detected drops in the primary drip chamber when the piggyback should be infusing. To reset this alarm, the problem causing the flow from the primary fluid source, such as the piggyback infusion source being located at or lower than the level of the primary fluid source or the inadvertent closure of the slide clamp on the IV tube connected to the piggyback fluid source, must be removed. The incomplete-program alarm indicates that the start key was pressed prior to entering or confirming a programming parameter. To reset this alarm, the missing parameter value and the "confirm settings" soft key, if required, must be entered. The reset-manual-release alarm indicates that the manual tube release has been activated. To reset this alarm, the manual tube release must be reset.

The tube-not-loaded alarm indicates that the IV tube has not been loaded prior to pressing the start key. To reset this alarm, the IV tube must be loaded. The out-of-range alarm indicates that a programming value outside of the preprogrammed allowable range has been entered. This alarm occurs when the "confirm settings" soft key or start key is pressed. To reset the out-of-range alarm, values within the preprogrammed range must be entered. The temperature-too-high alarm indicates that the operating temperature of the tube is outside design limits. To reset this alarm, the tube must be cooled by moving the pump to a suitable temperature environment. The temperature-too-low alarm means that the operating temperature of the tube is outside the design limits. To remove this alarm, the tube must be warmed by moving the pump to a suitable temperature environment. The tube-misload alarm indicates that the IV tube has been improperly loaded. To remove this alarm, the IV tube must be removed and reloaded properly. The tube-unload alarm indicates that the IV tube has not been removed from the tube-loading channel during an attempted tube-unloading procedure. If this occurs, the proper tube-unloading procedure should be employed or the manual tube release should be used.

The upstream-occlusion alarm indicates that an upstream occlusion, such as a closed proximal slide clamp, has occurred. To reset this alarm, the source of the occlusion must be removed. The container-empty alarm follows the container-empty alert condition described above. This alarm indicates that the container-empty alert condition has existed for a predetermined volume. To reset this alarm, a new fluid source container must be connected or the pump powered off. The no-slide-clamp alarm indicates that the on/off slide clamp has not been properly loaded. To reset this alarm, the tubing must be removed and reloaded, properly locating the on/off slide clamp in the keyed slot.

Figure 28A:
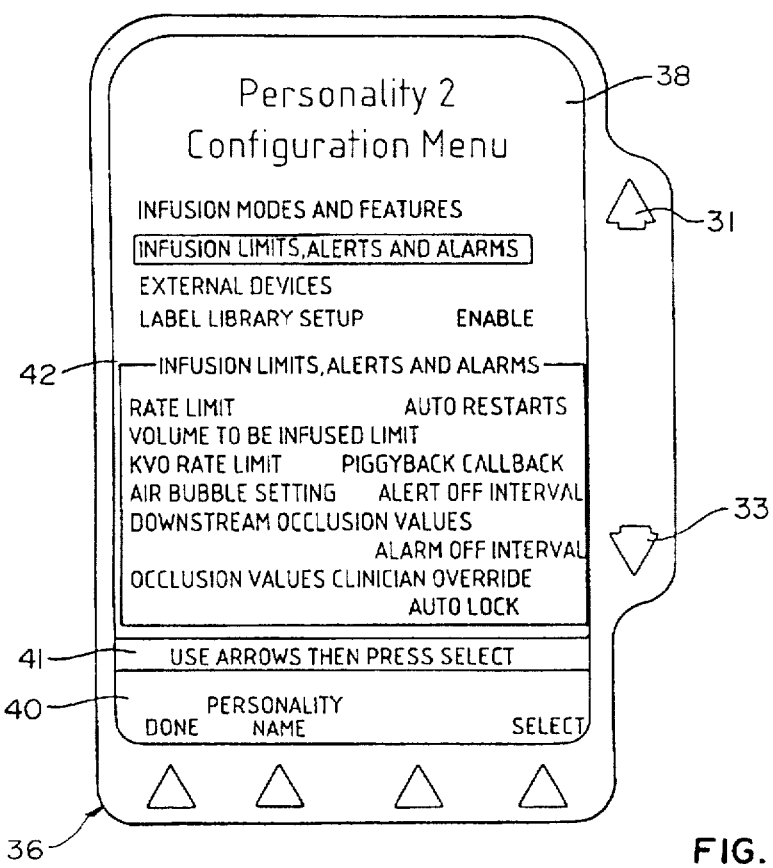
Figure 28B:
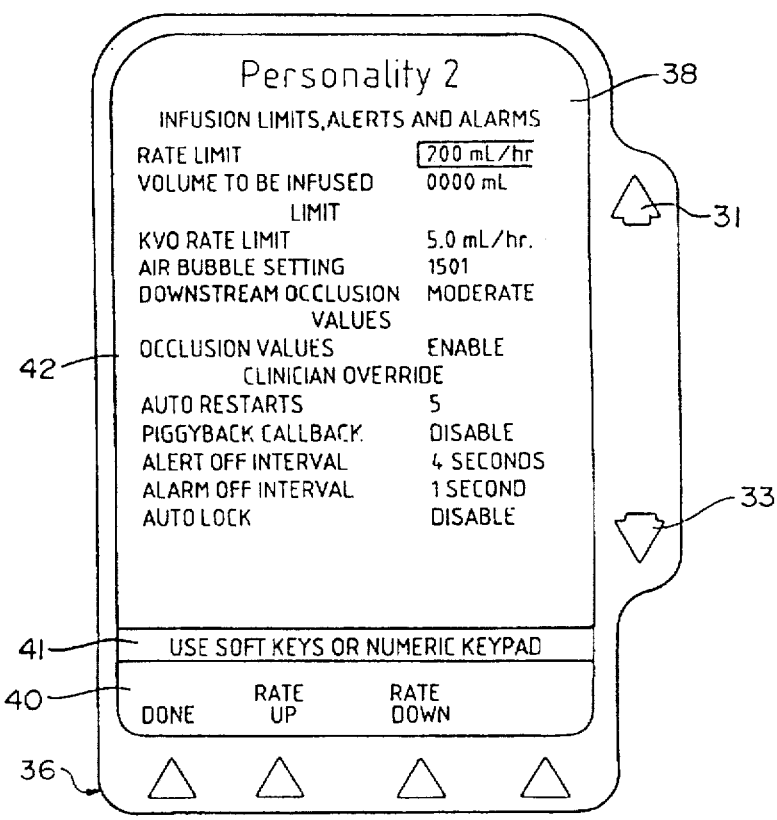

The authorized hospital personnel can program clinical feature limits and infusion alert and alarm characteristics. The infusion limits, alerts and alarms are accessed from the Personality™ configuration menu, seen in FIG. 28(a). Upon selection, the infusion limits, alerts and alarms menu seen in FIG. 28(b) is displayed. The settings in this menu apply to the infusion pump as a whole and are not programmable for separate channels.

Figure 29:
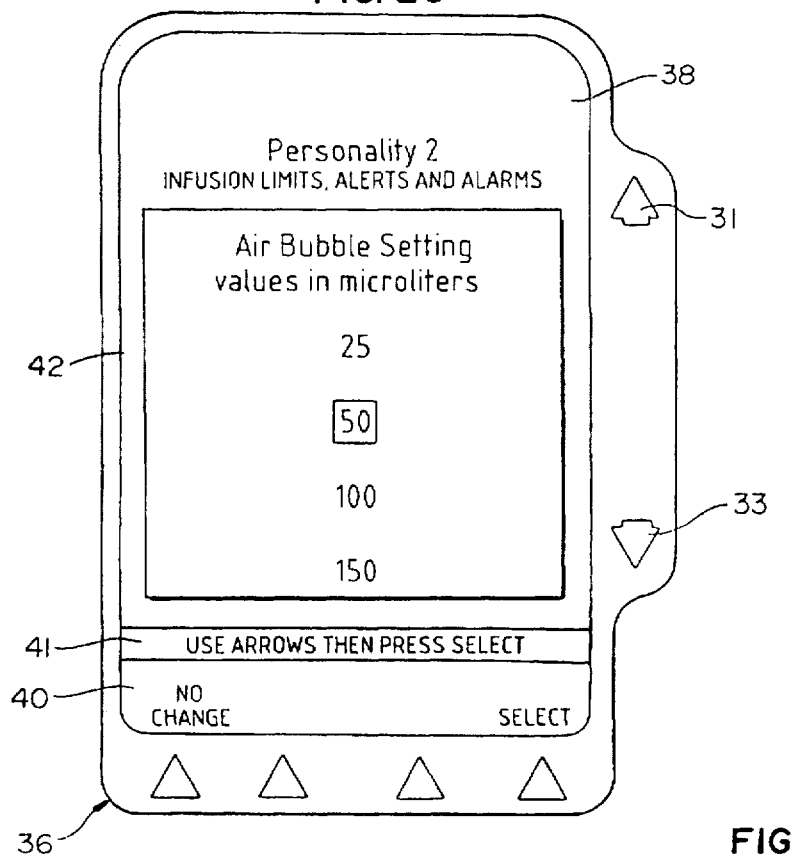

The authorized hospital personnel can adjust the flow rate limit, adjust the maximum volume to be infused, adjust the KVO rate, enable or disable a piggyback callback alert, adjust the time between audible tones for the alert and alarm, and enable or disable the auto-lock feature. The authorized hospital personnel also can set the size of the air bubble to be detected by the infusion pump. Referring to FIG. 29, an air bubble select pull-down menu which is displayed upon selection of the air bubble setting is seen. The screen includes a "no change" soft key and a "select" soft key. Options on the bubble size are displayed. In a preferred embodiment, four bubble size levels are displayed. In the preferred embodiment described herein, the four bubble size levels are 25 microL, 50 microL, 100 microL and 150 microL. Each bubble size level will detect air bubbles within a given range. For example, the 25 microL level will detect air bubbles above 25 microL and will not detect air bubbles below 10 microL; the 50 microL level will detect air bubbles above 50 microL and will not detect air bubbles below 25 microL; the 100 microL level will detect air bubbles above 100 microL and will not detect air bubbles below 50 microL; and the 150 microL level will detect air bubbles above 150 microL and will not detect air bubbles below 100 microL.

Figure 30:
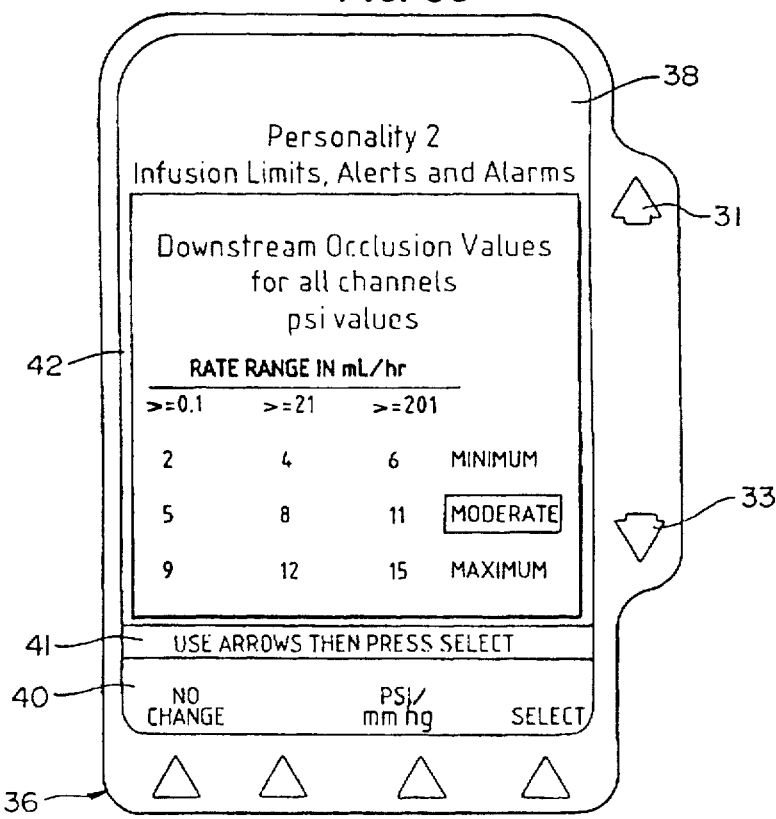

The authorized hospital personnel also can select a range of downstream occlusion values to be detected by the infusion pump. Referring to FIG. 30, a downstream occlusion value pulldown menu, which is displayed upon selection of the downstream occlusion values, is seen. The screen includes a "no change" soft key, a "PSI/MMHG" soft key which selects the units, and a "select" soft key. Options on the downstream occlusion values are displayed. In a preferred embodiment, three downstream occlusion values are displayed. In the preferred embodiment described herein, the three values are minimum, moderate and maximum. The minimum, moderate and maximum values indicate an approximate maximum pressure for different flow rate ranges. In the preferred embodiment, three flow rate ranges are indicated.

The authorized hospital personnel also can set whether the clinician can override the downstream occlusion values. When the occlusion value clinician override is highlighted in the infusion limits, alerts and alarm menu, an "enable/disable" soft key appears. The infusion pump also can be configured to include an auto-restart function. This function enables the infusion pump to automatically restart itself when a downstream occlusion has been corrected within a predetermined time, such as in the preferred embodiment, within one minute after detection. This is likely to occur if, for example, the downstream occlusion is caused by patient movement which subsequently opens the IV tube. The infusion pump will continue to attempt an auto restart for a given number of preselected occurrences before manual intervention is required. The authorized hospital personnel also can set the number of auto restarts that will occur after a downstream occlusion alarm occurs and is relieved. The authorized hospital personnel also can require that a clinician program a fluid delivery so that the fluid level in the drip chamber, in conjunction with a drop sensor, can provide a container-empty alert. When the drop sensor is highlighted in the configuration menu, a "mandatory/optional" soft key appears.

The infusion pump further includes service features which are accessible from the configuration/service menu. Upon selection of the service features, a service features menu is displayed. In the battery information selection, the slave microprocessor keeps track of a plurality of time periods related to battery operation. In the preferred embodiment, several parameters are tracked, including the total amount of time the infusion pump is on and not plugged in, the total amount of time the infusion pump was on. A battery information screen includes the battery charge icon 122, "done" and "clear times" soft keys, and the parameters. When a new battery is installed, the time on battery parameter is cleared. The service features also include sensor calibration, which displays information related to the installation or replacement of certain infusion pump components, and manufacturing tests, which are used in the manufacturing process to calibrate infusion pump components.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An infusion pump comprising:
a main body portion;
a display contained on the main body portion for displaying user interface information;
at least one pump module removably secured to the main body portion and adapted to receive a tube, the pump module having means for applying pumping action to the tube;
an auxiliary display contained on the pump module for displaying supplemental user interface information;
microprocessor means contained in the main body portion for generating user interface information on the display areas; and
means for generating a plurality of pictoral graphic representations as user interface information on the main display;
wherein a plurality of sets of configuration parameters are included as user interface information such that a user can select which of the plurality of sets of configuration parameters to configure the infusion pump.

2. The infusion pump of claim 1 wherein the display includes a status area, a prompt area, and a soft key label area and wherein the infusion pump further includes a plurality of soft keys contained in juxtaposition to the soft key label area.

3. The infusion pump of claim 1 further including means for entering values related to a beneficial agent to be infused into a patient and means responsive to the entered values for calculating a dose of the beneficial agent to be infused into the patient.

4. The infusion pump of claim 1 further including means for entering values related to a beneficial agent to be infused into a patient and means responsive to the entered values for calculating an infusion profile of the beneficial agent, wherein a pictoral graphic representation of the calculated infusion profile is included as user interface information, the pictoral graphic representation including the infusion remaining.

5. The infusion pump of claim 1 further including means for sensing tube restrictions wherein a pictoral graphic representation of the degree to which the tube is restricted is included as user interface information.

6. The infusion pump of claim 1 further including a battery which provides electrical power to the microprocessor means, the display and the means for applying pumping action; and means for detecting the charge of the battery, wherein a pictoral graphic representation of the charge of the battery is included as user interface information.

7. The infusion pump of claim 1 further including means for sensing the presence of air in the tube wherein a pictoral graphic representation of the presence of air in the tube is included as user interface information.

8. The infusion pump of claim 1 further wherein at least two pump modules are provided and the display includes user interface information for at least two pump modules.

21

9. The infusion pump of claim 1 wherein the microprocessor means further includes means for storing user interface information related to a specific patient.

10. The infusion pump of claim 1 further including means for clearing the stored user interface information for a specific patient.

11. An infusion pump comprising:

a main body portion;

a display contained on the main body portion;

at least one pump module removably secured to the main body portion and adapted to receive a tube, the pump module including means for applying pumping action to the tube;

microprocessor means for generating user interface information on the display;

means for entering values related to a beneficial agent to be infused into a patient; and wherein a pictoral graphic representation of the calculated infusion profile is included as user interface information, the pictoral graphic representation including the infusion remaining.

12. The infusion pump of claim 11 wherein the microprocessor means further includes means for storing user interface information related to a specific patient.

13. The infusion pump of claim 12 further including means for clearing the stored user interface information for a specific patient.

14. The infusion pump of claim 11 wherein the infusion profile includes a ramp up infusion period and a ramp down infusion period.

15. The infusion pump of claim 11 wherein the pictoral graphic representation includes a ramp up representation and a ramp down representation.

16. The infusion pump of claim 11 wherein the at least one pump module includes an auxiliary display for displaying supplemental user interface information.

17. The infusion pump of claim 11 further wherein a plurality of sets of configuration parameters is included as user interface information.

18. The infusion pump of claim 11 wherein the display includes a status area, a prompt area, and a soft key label area and wherein the infusion pump further includes a plurality of soft keys contained in juxtaposition to the soft key label area.

19. The infusion pump of claim 11 further including means for entering values related to a beneficial agent to be infused into a patient and means responsive to the entered values for calculating a dose of the beneficial agent to be infused into the patient.

20. The infusion pump of claim 11 further including means for sensing tube restrictions wherein a pictoral graphic representation of the degree to which the tube is restricted is included as user interface information.

21. The infusion pump of claim 11 further including a battery which provides electrical power to the microprocessor means, the display; and the means for applying pumping action and means for detecting the charge of the battery, wherein a pictoral graphic representation of the charge of the battery is included as user interface information.

22. The infusion pump of claim 11 further including means for sensing the presence of air in the tube wherein a pictoral graphic representation of the presence of air in the tube is included as user interface information.

23. The infusion pump of claim 11 further wherein at least two pump modules are provided and the display includes user interface information for at least two pump modules.

22

24. An infusion pump comprising:

a main body portion;

a display contained on the main body portion;

at least one pump module removably secured to the main body portion and adapted to receive a tube, the pump module including means for applying pumping action to the tube;

microprocessor means for generating user interface information on the display; and means for sensing tube restrictions;

wherein a pictoral graphic representation of the degree to which the tube is restricted is included as one of the plurality of pictoral graphic representations of user interface information.

25. The infusion pump of claim 24 wherein the microprocessor means further includes means for storing user interface information related to a specific patient.

26. The infusion pump of claim 25 further including means for clearing the stored user interface information for a specific patient.

27. The infusion pump of claim 24 wherein the pictoral graphic representation includes a plurality of triangles.

28. The infusion pump of claim 24 wherein the at least one pump module includes an auxiliary display for displaying supplemental user interface information.

29. The infusion pump of claim 24 further wherein a plurality of sets of configuration parameters is included as user interface information.

30. The infusion pump of claim 24 wherein the display includes a status area, a prompt area, and a soft key label area and wherein the infusion pump further includes a plurality of soft keys contained in juxtaposition to the soft key label area.

31. The infusion pump of claim 24 further including means for entering values related to a beneficial agent to be infused into a patient and means responsive to the entered values for calculating a dose of the beneficial agent to be infused into the patient.

32. The infusion pump of claim 24 further including means for entering values related to a beneficial agent to be infused into a patient and means responsive to the entered values for calculating an infusion profile of the beneficial agent, wherein a pictoral graphic representation of the calculated infusion profile is included as user interface information, the pictoral graphic representation including the infusion remaining.

33. The infusion pump of claim 24 further including a battery which provides electrical power to the microprocessor means, the display; and the means for applying pumping action and means for detecting the charge of the battery, wherein a pictoral graphic representation of the charge of the battery is included as user interface information.

34. The infusion pump of claim 24 further including means for sensing the presence of air in the tube wherein a pictoral graphic representation of the presence of air in the tube is included as user interface information.

35. The infusion pump of claim 24 further wherein at least two pump modules are provided and the display includes user interface information for at least two pump modules.

36. An infusion pump comprising:

a main body portion;

a display contained on the main body portion;

at least one pump module removably secured to the main body portion and adapted to receive a tube, the pump module including means for applying pumping action to the tube;

microprocessor means for generating user interface information on the display;

a battery which provides electrical power to the microprocessor means, the display, and the means for applying pumping action; and means for determining the charge of the battery;

wherein a pictoral graphic representation of the charge of the battery is included as user interface information.

37. The infusion pump of claim 36 wherein the microprocessor means further includes means for storing user interface information related to a specific patient.

38. The infusion pump of claim 37 further including means for clearing the stored user interface information for a specific patient.

39. The infusion pump of claim 36 wherein the at least one pump module includes an auxiliary display for displaying supplemental user interface information.

40. The infusion pump of claim 36 further wherein a plurality of sets of configuration parameters is included as user interface information.

41. The infusion pump of claim 36 wherein the display includes a status area, a prompt area, and a soft key label area and wherein the infusion pump further includes a plurality of soft keys contained in juxtaposition to the soft key label area.

42. The infusion pump of claim 36 further includes means for entering values related to a beneficial agent to be infused into a patient and means responsive to the entered values for calculating a dose of the beneficial agent to be infused into the patient.

43. The infusion pump of claim 36 further including means for entering values related to a beneficial agent to be infused into a patient and means responsive to the entered values for calculating an infusion profile of the beneficial agent, wherein a pictoral graphic representation of the calculated infusion profile is included as user interface information, the pictoral graphic representation including the infusion remaining.

44. The infusion pump of claim 36 further including means for sensing tube restrictions wherein a pictoral graphic representation of the degree to which the tube is restricted is included as user interface information.

45. The infusion pump of claim 36 further including means for sensing the presence of air in the tube wherein a pictoral graphic representation of the presence of air in the tube is included as user interface information.

46. The infusion pump of claim 36 further wherein at least two pump modules are provided and the display includes user interface information for at least two pump modules.

\* \* \* \* \*